US012655472B2

(12) United States Patent
Kang et al.

(10) Patent No.:    US 12,655,472 B2
(45) Date of Patent:       Jun. 16, 2026

(54) MICROBE DETECTION METHOD USING FISH ANALYSIS

(71) Applicant: BElement Inc., Ulsan (KR)

(72) Inventors: Joo Hun Kang, Ulsan (KR); Taejoon Kwon, Ulsan (KR); Hajin Kim, Ulsan (KR); Sungho Kim, Ulsan (KR); Minseok Lee, Ulsan (KR); Hwi Hyun, Ulsan (KR); Hwa Soo Ko, Ulsan (KR)

(73) Assignee: BElement Inc., Ulsan (KR)

( * ) Notice: Subject to any disclaimer, the term of this patent is extended or adjusted under 35 U.S.C. 154(b) by 582 days.

(21) Appl. No.: 18/037,307

(22) PCT Filed: Dec. 24, 2020

(86) PCT No.: PCT/KR2020/019154
§ 371 (c)(1),
(2) Date: Nov. 14, 2023

(87) PCT Pub. No.: WO2022/102865
PCT Pub. Date: May 19, 2022

(65) Prior Publication Data
US 2025/0188523 A1      Jun. 12, 2025

(30) Foreign Application Priority Data

Nov. 16, 2020    (KR) ........................ 10-2020-0153079
Dec. 22, 2020    (KR) ........................ 10-2020-0181346

(51) Int. Cl.
*C12Q 1/68*            (2018.01)
*C12Q 1/6837*          (2018.01)
*C12Q 1/6841*          (2018.01)

(52) U.S. Cl.
CPC ......... *C12Q 1/6841* (2013.01); *C12Q 1/6837* (2013.01)

(58) Field of Classification Search
CPC .................................. C12Q 1/68; C12N 15/00
See application file for complete search history.

(56) References Cited

U.S. PATENT DOCUMENTS 6,656,687 B1    12/2003  Hyldig-Nielsen
9,657,327 B2     5/2017  Metzger et al.
(Continued)

FOREIGN PATENT DOCUMENTS

JP      2002-0543800       12/2002
KR    10-2012-0133385      12/2012
(Continued)

OTHER PUBLICATIONS

Sato, Microdevice in Cellular Pathology: Microfluidic Platforms for Fluorescence in situ Hybridization and Analysis of Circulating Tumor Cells, Anal Sci. 2015;31(9):867-73. doi: 10.2116/analsci.31. 867.*

(Continued)

*Primary Examiner* — Aaron A Priest
(74) *Attorney, Agent, or Firm* — Klarquist Sparkman, LLP

(57)         ABSTRACT

The present invention relates to a microbe detection method using FISH analysis. More specifically, the present invention relates to a multiple detection method for microbes by using FISH analysis, a method for providing information about diagnosis of an infectious disease, a method for assaying sensitivity of microbes to an antibacterial agent, a method for detecting or identifying a microbe, and a method for enhancing efficiency of FISH analysis. In addition, the present invention relates to a composition for detecting or identifying a microbe used for FISH analysis.

15 Claims, 27 Drawing Sheets
Specification includes a Sequence Listing.

(56) References Cited

U.S. PATENT DOCUMENTS

| | | | |
|---|---|---|---|
| 9,845,493 B2 | 12/2017 | Brenner et al. | |
| 2003/0032007 A1 | 2/2003 | Snaidr | |
| 2016/0054308 A1 | 2/2016 | Guo | |
| 2016/0160268 A1 | 6/2016 | Haake et al. | |
| 2016/0273025 A1 | 9/2016 | Almeida et al. | |
| 2017/0220733 A1* | 8/2017 | Zhuang | C12N 15/1065 |
| 2017/0328900 A1* | 11/2017 | Stroot | G01N 33/56911 |
| 2019/0119728 A1 | 4/2019 | Gomez et al. | |
| 2020/0010874 A1 | 1/2020 | Wang et al. | |
| 2023/0076434 A1* | 3/2023 | Geva-Zatorsky | A61K 36/02 |
| 2023/0241603 A1* | 8/2023 | Straus | G01N 33/54333 422/501 |

FOREIGN PATENT DOCUMENTS

| | | | |
|---|---|---|---|
| KR | 10-1810786 | 12/2017 | |
| KR | 10-20200005873 | 1/2020 | |
| KR | 10-2084688 | 3/2020 | |
| KR | 10-20220006810 | 1/2022 | |
| WO | WO 2010/048511 | 4/2010 | |
| WO | WO 2011/106536 | 9/2011 | |
| WO | WO-2020073019 A2 * | 4/2020 | G01N 33/54333 |

OTHER PUBLICATIONS

Lee et al., Quantitative Fluorescence In Situ Hybridization (FISH) of Magnetically Confined Bacteria Enables Early Detection of Human Bacteremia, Small Methods. Mar. 2022;6(3):e2101239. doi: 10.1002/smtd.202101239. Epub Feb. 3, 2022.*

Liu et al, Microfluidic fluorescence in situ hybridization and flow cytometry (μFlowFISH), Lab Chip. Aug. 21, 2011;11(16):2673-9. doi: 10.1039/c1lc20151d. Epub Jul. 14, 2011.*

International Search Report (ISR) and Written Opinion for Application No. PCT/KR2020/019154, mailed Mar. 23, 2022, 19 pages (with English translation of the ISR).

Mondal et al., "Highly multiplexed single-cell in situ RNA and DNA analysis with biorthogonal cleavable fluorescent oligonucleotides," *Chem. Sci.*, vol. 9, pp. 2909-2917 (2018).

Mondal et al., "Highly Multiplexed Single-Cell in Situ Protein Analysis with Cleavable Fluorescent Antibodies," *Agnew. Chem. Int. Ed.*, vol. 56, pp. 1-5 (2017).

Notice of Allowance for KR Application No. 10-2020-018346, dated Apr. 21, 2023, 11 pages (with English translation).

Office Action for KR Application No. 10-2020-0153079, dated Aug. 28, 2022, 14 pages (with English translation).

Office Action for KR Application No. 10-2020-0181346, dated Oct. 10, 2020, 18 pages (with English translation).

Syal, et al., "Current and emerging techniques for antibiotic susceptibility tests," *Theranostics*, vol. 7(7), pp. 1795-1805 (2017).

* cited by examiner

DAPI

Cy3

Cy5

Merge

DAPI

Cy5

Merge

For 1 hour, 37 degree C
With antibiotics

Gentamicin, Neomycin, Tobramycin,
Cefotaxime, Ciprofloxacin
($OD_{600}$ 0.4 ~ 1.0)

Log-phase culture
($OD_{600}$ ~ 0.6)

Without antibiotics

No Antibiotics
($OD_{600}$ > 1.0)

DNA FISH 12 hours                    PNA FISH 5 min

*Target species: *S. aureus*

DNA FISH 12 hours

PNA FISH 5 min

*Target species: *S. aureus*

100 nM Disulfide Cy3 PNA
Probe Target: *E. coli*

(SEQ ID NO: 29) FIRST PROBE     Cy3     Cy5 SECOND PROBE  (SEQ ID NO: 31)

3'-TCCTTCCCTCATTTC-5'  3'-AATTATGGAAACGAG-5'

5'-.....CGGGGAGGAAGGGAGTAAAG.........TTAATACCTTTGCTCATTG.......-3'

(SEQ ID NO: 30) *E. coli*  TARGET SEQUENCE   (SEQ ID NO: 32)

SEQUENCE LISTING

<160> NUMBER OF SEQ ID NOS: 28

<210> SEQ ID NO 1

-continued

```
<211> LENGTH: 15
<212> TYPE: DNA
<213> ORGANISM: Artificial Sequence
<220> FEATURE:
<223> OTHER INFORMATION: PNA probe 1

<400> SEQUENCE: 1
aggaagggag taaag                                                    15

<210> SEQ ID NO 2
<211> LENGTH: 15
<212> TYPE: DNA
<213> ORGANISM: Artificial Sequence
<220> FEATURE:
<223> OTHER INFORMATION: PNA probe 2

<400> SEQUENCE: 2
gcggtagcac agaga                                                    15

<210> SEQ ID NO 3
<211> LENGTH: 15
<212> TYPE: DNA
<213> ORGANISM: Artificial Sequence
<220> FEATURE:
<223> OTHER INFORMATION: PNA probe 3

<400> SEQUENCE: 3
agcggtagca cagag                                                    15

<210> SEQ ID NO 4
<211> LENGTH: 15
<212> TYPE: DNA
<213> ORGANISM: Artificial Sequence
<220> FEATURE:
<223> OTHER INFORMATION: PNA probe 4

<400> SEQUENCE: 4
gagcggtagc acaga                                                    15

<210> SEQ ID NO 5
<211> LENGTH: 15
<212> TYPE: DNA
<213> ORGANISM: Artificial Sequence
<220> FEATURE:
<223> OTHER INFORMATION: PNA probe 5

<400> SEQUENCE: 5
atgccatcag atgtg                                                    15

<210> SEQ ID NO 6
<211> LENGTH: 15
<212> TYPE: DNA
<213> ORGANISM: Artificial Sequence
<220> FEATURE:
<223> OTHER INFORMATION: PNA probe 6

<400> SEQUENCE: 6
catgccatca gatgt                                                    15

<210> SEQ ID NO 7
<211> LENGTH: 15
<212> TYPE: DNA
<213> ORGANISM: Artificial Sequence
<220> FEATURE:
<223> OTHER INFORMATION: PNA probe 7

<400> SEQUENCE: 7
```

-continued

```
ggcctcatgc catca                                         15

<210> SEQ ID NO 8
<211> LENGTH: 15
<212> TYPE: DNA
<213> ORGANISM: Artificial Sequence
<220> FEATURE:
<223> OTHER INFORMATION: PNA probe 8

<400> SEQUENCE: 8
aacggacgag aagct                                         15

<210> SEQ ID NO 9
<211> LENGTH: 15
<212> TYPE: DNA
<213> ORGANISM: Artificial Sequence
<220> FEATURE:
<223> OTHER INFORMATION: PNA probe 9

<400> SEQUENCE: 9
aagtgaaaga cggtc                                         15

<210> SEQ ID NO 10
<211> LENGTH: 15
<212> TYPE: DNA
<213> ORGANISM: Artificial Sequence
<220> FEATURE:
<223> OTHER INFORMATION: PNA probe 10

<400> SEQUENCE: 10
cctgagggag aaagt                                         15

<210> SEQ ID NO 11
<211> LENGTH: 15
<212> TYPE: DNA
<213> ORGANISM: Artificial Sequence
<220> FEATURE:
<223> OTHER INFORMATION: PNA probe 11

<400> SEQUENCE: 11
ctactgagct agagt                                         15

<210> SEQ ID NO 12
<211> LENGTH: 15
<212> TYPE: DNA
<213> ORGANISM: Artificial Sequence
<220> FEATURE:
<223> OTHER INFORMATION: PNA probe 12

<400> SEQUENCE: 12
aacgcttctt tcctc                                         15

<210> SEQ ID NO 13
<211> LENGTH: 15
<212> TYPE: DNA
<213> ORGANISM: Artificial Sequence
<220> FEATURE:
<223> OTHER INFORMATION: PNA probe 13

<400> SEQUENCE: 13
tctttcctcc cgagt                                         15

<210> SEQ ID NO 14
<211> LENGTH: 15
<212> TYPE: DNA
```

```
<213> ORGANISM: Artificial Sequence
<220> FEATURE:
<223> OTHER INFORMATION: PNA probe 14

<400> SEQUENCE: 14
agaagaacaa ggacg                                                    15

<210> SEQ ID NO 15
<211> LENGTH: 15
<212> TYPE: DNA
<213> ORGANISM: Artificial Sequence
<220> FEATURE:
<223> OTHER INFORMATION: PNA probe 15

<400> SEQUENCE: 15
gcactatcgg atgaa                                                    15

<210> SEQ ID NO 16
<211> LENGTH: 15
<212> TYPE: DNA
<213> ORGANISM: Artificial Sequence
<220> FEATURE:
<223> OTHER INFORMATION: PNA probe 16

<400> SEQUENCE: 16
aaaaggtgca cttgc                                                    15

<210> SEQ ID NO 17
<211> LENGTH: 15
<212> TYPE: DNA
<213> ORGANISM: Artificial Sequence
<220> FEATURE:
<223> OTHER INFORMATION: PNA probe 17

<400> SEQUENCE: 17
cttgcatcac tacca                                                    15

<210> SEQ ID NO 18
<211> LENGTH: 15
<212> TYPE: DNA
<213> ORGANISM: Artificial Sequence
<220> FEATURE:
<223> OTHER INFORMATION: PNA probe 18

<400> SEQUENCE: 18
ccgcatggtt ttgat                                                    15

<210> SEQ ID NO 19
<211> LENGTH: 15
<212> TYPE: DNA
<213> ORGANISM: Artificial Sequence
<220> FEATURE:
<223> OTHER INFORMATION: PNA probe 19

<400> SEQUENCE: 19
accgcataag agaga                                                    15

<210> SEQ ID NO 20
<211> LENGTH: 15
<212> TYPE: DNA
<213> ORGANISM: Artificial Sequence
<220> FEATURE:
<223> OTHER INFORMATION: PNA probe 20

<400> SEQUENCE: 20
cgcataagag agact                                                    15
```

<210> SEQ ID NO 21
<211> LENGTH: 15
<212> TYPE: DNA
<213> ORGANISM: Artificial Sequence
<220> FEATURE:
<223> OTHER INFORMATION: PNA probe 21

<400> SEQUENCE: 21
ccgcataaca atgga                                                  15

<210> SEQ ID NO 22
<211> LENGTH: 15
<212> TYPE: DNA
<213> ORGANISM: Artificial Sequence
<220> FEATURE:
<223> OTHER INFORMATION: PNA probe 22

<400> SEQUENCE: 22
cgcataacaa tggat                                                  15

<210> SEQ ID NO 23
<211> LENGTH: 15
<212> TYPE: DNA
<213> ORGANISM: Artificial Sequence
<220> FEATURE:
<223> OTHER INFORMATION: PNA probe 23

<400> SEQUENCE: 23
tgaaagatgc aagcg                                                  15

<210> SEQ ID NO 24
<211> LENGTH: 15
<212> TYPE: DNA
<213> ORGANISM: Artificial Sequence
<220> FEATURE:
<223> OTHER INFORMATION: PNA probe 24

<400> SEQUENCE: 24
caagaacgtg tgtga                                                  15

<210> SEQ ID NO 25
<211> LENGTH: 15
<212> TYPE: DNA
<213> ORGANISM: Artificial Sequence
<220> FEATURE:
<223> OTHER INFORMATION: PNA probe 25

<400> SEQUENCE: 25
tgagtcttgt agagg                                                  15

<210> SEQ ID NO 26
<211> LENGTH: 24
<212> TYPE: DNA
<213> ORGANISM: Artificial Sequence
<220> FEATURE:
<223> OTHER INFORMATION: common probe

<400> SEQUENCE: 26
ggtgtgacgg gcggtgtgta caag                                        24

<210> SEQ ID NO 27
<211> LENGTH: 30
<212> TYPE: DNA
<213> ORGANISM: Artificial Sequence
<220> FEATURE:

-continued

```
<223> OTHER INFORMATION: E. coli 16s rRNA-specific probe

<400> SEQUENCE: 27
ggtaagcgcc ctcccgaagg ttaagctacc                                        30

<210> SEQ ID NO 28
<211> LENGTH: 32
<212> TYPE: DNA
<213> ORGANISM: Artificial Sequence
<220> FEATURE:
<223> OTHER INFORMATION: S. aureus 16s rRNA-specific probe

<400> SEQUENCE: 28
gggatttgct tgacctcgcg gtttcgctgc cc                                     32
```

MICROBE DETECTION METHOD USING FISH ANALYSIS

CROSS REFERENCE TO RELATED APPLICATIONS

This is the U.S. National Stage of International Application No. PCT/KR2020/019154, filed Dec. 24, 2020, which claims the benefit of Korean Patent Application No. 10-2020-0153079, filed Nov. 16, 2020, and Korean Patent Application No. 10-2020-0181346, filed Dec. 22, 2020.

INCORPORATION OF ELECTRONIC SEQUENCE LISTING

The electronic sequence listing, submitted herewith as a .txt file named UA-63912-US Sequence Listing Revised 260227.txt (6,985 bytes), created on Feb. 26, 2026, is herein incorporated by reference in its entirety.

TECHNICAL FIELD

The present disclosure relates to a method of detecting microorganisms using Fluorescence in situ hybridization (FISH) analysis. Specifically, the present disclosure relates to a multi-detection method for microorganisms, a method of providing information on the diagnosis of infectious diseases, a method of evaluating antibiotic susceptibility of microorganisms, and a method of detecting or identifying microorganisms, and a method of increasing the efficiency of FISH analysis, using FISH analysis. In addition, the present disclosure relates to a composition for detecting or identifying microorganisms used in FISH analysis. This patent application claims priority over Korean Patent Application No. 20-153079, filed with the Korean Intellectual Property Office on Nov. 16, 2020, and Korean Patent Application No. 20-181346, filed with the Korean Intellectual Property Office on Dec. 22, 2020, and the disclosure of the patent application is incorporated herein by reference.

BACKGROUND ART

In general, as a method of diagnosing pathogenic microorganisms, a method of observing using a microscope, an immunological method of detecting a specific antigen of a pathogenic microorganism, and a method of amplifying a specific gene using PCR technology are used. However, in order to apply the microscopic observation method, the pathogen must be large enough to be observed with a general microscope, and dense enough to be easily found in the specimen, and the shape thereof must be clearly distinguishable from other organisms. That is, in the case of microscopic organisms such as viruses or bacteria having similar shapes, it is difficult to accurately diagnose using a microscope. In addition, in the case of immunological methods tracking antigens of pathogenic microorganisms, although the causative organism may be accurately diagnosed, the density of the causative pathogenic microorganisms needs to be sufficiently high, and it is not always possible to obtain antibodies to the unique antigens of all pathogenic microorganisms. In addition, the PCR method of amplifying a specific gene present only in pathogenic microorganisms and then confirming the existence of the gene for diagnosis enables accurate diagnosis. However, since the PCR method requires a gene amplification process, it is greatly influenced by various factors. For example, impurities remaining in the process of purifying genetic material may hinder amplification or cause non-specific amplification, and the process of purifying genetic materials and amplifying genes is time-consuming and expensive, requiring expensive precision instruments and skilled professionals. Therefore, to obtain high concentrations of pathogenic microorganisms without amplifying genes, microorganisms are sometimes cultured. However, the culturing is difficult since it is not easy to know the culture conditions of microorganisms before identifying them. In addition, in the case of the method of detecting microorganisms using fluorescent staining immunologically, microorganisms cannot be selectively detected.

In order to solve this problem, a fluorescence in situ hybridization (FISH) method is used. FISH refers to a technology capable of detecting microorganisms through fluorescence microscopy by hybridizing a microorganism with a probe having a fluorescent material attached thereto. In the case of conventional FISH technology, the efficiency of probe entry into cells differs depending on the type or characteristics of the cell, so that the analysis efficiency varies greatly; the analysis time is very long because the process of hybridization and non-hybridization between the probe and the microorganism takes a lot of time, so that the analysis efficiency is substantially reduced; and these factors lead to a limitation in realizing multiple analyzes and a decrease in analysis accuracy. Therefore, there is a demand for development of a method capable of rapidly and accurately detecting various types of microorganisms by improving FISH efficiency.

Under this background, various studies on microorganism detection methods using fluorescent signals are being actively conducted (Korean Patent Registration No. 10-1106616), but the research results are still poor.

DETAILED DESCRIPTION OF THE DISCLOSURE

Technical Problem

One objective of the present disclosure is to provide a multi-detection method for microorganisms using fluorescence in situ hybridization (FISH) analysis.

Another objective of the present disclosure is to provide a method of providing information on the diagnosis of infectious diseases using FISH analysis.

Another objective of the present disclosure is to provide a method of improving the efficiency of FISH analysis.

Another objective of the present disclosure is to provide a method of evaluating the antibiotic susceptibility of microorganisms using FISH analysis.

Another objective of the present disclosure is to provide a method of detecting or identifying microorganisms using FISH analysis using a degradable probe which is linked to a detection label via a degradable covalent bond.

Another objective of the present disclosure is to provide a composition for detecting or identifying microorganisms, the composition including a degradable probe which is linked to a detection label via a degradable covalent bond used in FISH analysis.

However, the technical issues that the present disclosure is intended to address are not limited to those described above, and other issues not mentioned will be apparent to one of ordinary skill in the art from the following description.

Technical Solution to Problem

An embodiment of the present disclosure provides a multi-detection method for microorganisms including concentrating or fixing microorganisms included in a sample, and hybridizing labeled probes with the microorganisms by sequentially contacting the same with the microorganisms, and detecting signals respectively emitted from the sequentially hybridized probes.

The multi-detection method for microorganisms includes concentrating or fixing microorganisms included in a sample.

The term "sample" used herein may include a biological sample, an environmental sample, or a food sample.

The biological sample may refer to a sample obtained from a biological subject, including a sample derived from a biological tissue or body fluid obtained in vivo or in vitro. In an embodiment, the biological sample may be a bodily fluid (e.g., blood, plasma, serum, saliva, sputum, or urine), organs, tissues, fractions, and cells isolated from mammals, including humans, and is not limited thereto. The sample may also include extracts from biological samples, such as antibodies, proteins, and the like from biological fluids (e.g., blood or urine).

The environmental sample may include a water quality sample or a soil sample.

The sample may contain microorganisms.

In the method, the concentrating or fixing may further include contacting the sample and the magnetic particles so that the microorganisms included in the sample bind to the magnetic particles. The "fixing" may refer to attaching or fixing microorganisms to a specific location or region.

The "magnetic particle" used herein may refer to a particle exhibiting paramagnetic properties. Paramagnetism refers to the property of being weakly magnetized in the direction of a magnetic field when a magnetic field is present. The magnetic particles may be manufactured through known methods or commercially sold. The magnetic particles may be magnetic nanoparticles having a small diameter. In addition, the magnetic particles may have a diameter of about 1 nm to about 30,000 nm, about 1 nm to about 10,000 nm, about 1 nm to about 1,000 nm, about 1 nm to about 500 nm, about 50 nm to about 400 nm, or about 100 nm to about 300 nm. However, the diameter thereof is limited thereto. The magnetic material of the magnetic particles may be a magnetic metal or a magnetic metal oxide (e.g., metal oxide such as iron oxide). The magnetic metal may include: at least one metal selected from an iron group element (Fe, Ni, Co, etc.), a rare earth element (La, Ce, Pr, Nd, Pm, Sm, Eu, Gd, Tb, Dy, Ho, Er, Tm, Yb, Lu, etc.), a numismatic metal element (Cu, Ag, Au, etc.), a zinc group element (Zn, Cd, Hg, etc.), an aluminum group element (Al, Ga, In, Tl, etc.), an alkaline earth element (Ca, Sr, Ba, Ra, etc.), and a platinum group element (Pt, Pd, etc.); and alloys thereof. The type of the magnetic particles of an embodiment may include, for example, at least one selected from the group consisting of Co, Mn, Fe, Ni, Gd, Mo, $MM'_2O_4$, and MpOq. In this regard, M and M' may each indicate Co, Fe, Ni, Mn, Zn, Gd, or Cr, $0<p\leq3$, and $0<q\leq5$.

A microbial attachment factor may be coated on the surface of the magnetic particles. The term "microbial attachment factor" used herein refers to a factor capable of binding (attaching) to glycoproteins or carbohydrates on the surface of various microorganisms such as viruses, bacteria, and protozoa, and may be, for example, an antibody, a fragment of an antibody, an aptamer, a nucleic acid, a peptide, a protein, or any compound, each of which is capable of binding to any of various types of microorganisms. The microbial attachment factor may be, for example, at least one selected from the group consisting of mannose binding lectin (MBL), C-reactive protein (CRP), opsonin, CD14, toll-like receptor 4 (TLR4), neutrophil extracellular trap (NET), and a cytokine receptor.

When various types of microbial attachment factors that may bind to various types of microorganisms are coated on the surfaces of the magnetic particles, the magnetic particles may bind to any microorganisms included in the sample through the microbial attachment factors.

When a target microbial attachment factor that may bind to a specific type of microorganisms is coated on the surface of the magnetic particles, the magnetic particles may bind to specific microorganisms included in the sample through the target microbial attachment factor.

In the contacting the sample with the magnetic particles so that the microorganisms included in the sample bind to the magnetic particles, a magnetic field may be applied to the sample including the microorganisms bonded with the magnetic particles to fix the microorganisms. That is, the microorganisms may be fixed on a specific position or region by applying a magnetic field to the sample including the microorganisms bonded with the magnetic particles. The magnetic field may be formed in any conventional way. For example, the formation of the magnetic field may be performed using a magnet such as an electromagnet or a permanent magnet by electromagnetic induction. One or more magnets may be included, and may be applied in various arrangements such as in a series manner, a parallel manner, or a circular manner. Since the application of the magnetic field is not affected by environmental factors such as pH, temperature, and ions, stability is excellent.

In an embodiment of the present disclosure, the sample is brought into contact with the magnetic particles coated with the microbial attachment factor to allow the microorganisms included in the sample to bind to the magnetic particles. By fixing the magnetic particles by applying a magnetic field to the sample including the magnetic particles to which the microorganisms are bound, the microorganisms included in the sample are fixed together with the magnetic particles so that microorganisms may be separated from the rest of the sample except for the microorganisms, thus concentrating the microorganisms in the sample. In addition, since microorganisms are be fixed, multiple detection of microorganisms may be performed by sequentially contacting the probe.

The multi-detection method for microorganisms includes sequentially contacting labeled probes with the microorganisms to hybridize the same with the microorganisms, and detecting signals respectively emitted from the sequentially hybridized probes.

The detecting the signal may include, after detecting the signal emitted from one probe hybridized with the microorganisms, before hybridizing the other probe, washing the one probe. The washing may be performed with any sample used for washing a probe in the art, and may be performed with, for example, a solution containing formamide. The concentration of the formamide may be determined by those skilled in the art according to purpose, and may be about 10% (v/v) to about 90% (v/v), or about 40% (v/v) to about 80% (v/v).

The washing may be repeated once or twice or more.

The washing may be performed with a formamide solution at about 70° C. to about 75° C.

By the washing, one probe bound to the microorganisms may be removed. After washing, 10% or less probe may remain compared to that before washing. For example, 10%, 9%, 8%, 7%, 6%, 5%, 4%, 3%, 2%, 1%, or 0% probe may remain.

By effectively removing one probe bound to the micro-organisms by the washing, noise is not generated even after hybridization with the other probe, and thus microorganisms may be detected with high sensitivity, high specificity, and high reproducibility.

The one probe and the other probe may be different probes capable of sequentially hybridizing to two or more different types of microorganisms in the sample. In an embodiment, the probe may be the same probe capable of repeatedly hybridizing with the same type of microorganisms in the sample. In an embodiment, the probe may be the same probe capable of hybridizing to the same region in two or more different microorganisms in the sample. In an embodiment, the probes may be different probes capable of hybridizing to different regions of the same type of microorganisms in the sample.

The same probe may be labeled with the same or different labeling materials. In an embodiment, the different probes may be labeled with the same or different labeling materials.

In the method described above, the labeled probe may be labeled with a fluorescent material, a chromogenic substance, or a chemiluminescent substance. By labeling the probe with a labeling material, such as a fluorescent material, a chromogenic substance, or a chemiluminescent substance, microorganisms may be visualized (or imaged) and detected.

The fluorescent material may include one or more types of fluorescent materials selected from the group consisting of FAM, VIC, HEX, Cy5, Cy3, SYBR Green, DAPI, TAMRA, FITC, RITC, rhodamine, Fluoredite, FluorePrime, and ROX, and is not limited thereto. When a probe labeled with such a fluorescent material is used, hybridization and dissociation may be easily confirmed only by simple imaging by fluctuations in each fluorescence signal.

The chromogenic substance may include horse radish peroxidase (HRP), alkaline phosphatase (ALP), β-D-galactosidase (β-Gal), and the like, and is not limited thereto.

The chemiluminescent substance may include GFP, luciferin, etc., and is not limited thereto.

In regard to the method, the "probe" may be a part of the microorganism, for example, a polysaccharide expressed on the surface of the microorganism; a genetic material (DNA, RNA, etc.) in the microorganism; an antibody, an aptamer, DNA, RNA, peptide nucleic acid (PNA), oligosaccharides, peptides, or proteins, each of which binds to a protein of the microorganism.

In regard to the method, the detecting the signal emitted from the hybridized probe may be performed by a method known in the art, for example, histochemistry, immunohistochemistry, immunofluorescence, color-in-situ hybridization, Fluorescence in situ hybridization (FISH), and the like.

The presence or absence of microorganisms or the type of microorganisms may be determined by comparing the signal of the part where the signal emitted from the probe hybridized with the microorganisms exists and the signal of the other part. In addition, by comparison using a standard sample containing microorganisms having a known concentration in advance, the concentration of microorganisms included in the sample may be obtained.

In regard to the method, the culturing the microorganisms or the amplifying the genetic material of the microorganisms may not be included. In general, since microorganisms contained in biological samples, environmental samples, or food samples are often trace amounts, the conventional method of combining a labeled probe with microorganisms and measuring a signal emitted from the labeled probe has low efficiency. In order to increase the measurement efficiency, technologies for purifying microorganisms in samples, amplifying genetic material of microorganisms by methods such as PCR, or culturing microorganisms are used. However, transformation may occur during the process of purifying microorganisms; the amplification of genetic materials takes a long time and, when genetic information is not known, cannot be used; and when unknown microorganisms or a large number of microorganisms are included, it is difficult to set culture conditions. However, according to an embodiment of the method, since the microorganisms may be concentrated or fixed by attaching the microorganisms to the magnetic particles and separating the magnetic particles by a magnetic field, microorganisms may be efficiently detected without inclusion of culturing the microorganisms or amplifying the genetic material of the microorganisms.

In regard to the method, the microorganisms may include a bacterium, a virus, a mold, a fungus, or a combination thereof.

An embodiment of the present disclosure provides a method of providing information on the diagnosis of infectious diseases, the method including concentrating or fixing microorganisms included in a sample, and hybridizing labeled probes with the microorganisms by sequentially contacting the same with the microorganisms, and detecting signals respectively emitted from the sequentially hybridized probes.

The information providing method may include determining the presence or absence of microorganisms or the type of microorganisms by using information about a probe from which a signal is emitted.

For example, in the case where a probe specific to E. coli is used, when a signal is emitted from the probe, the type of microorganisms contained in the sample may be determined as being E. coli. By determining the type of microorganisms included in the sample, it is possible to provide information about the likelihood of developing an infectious disease, the onset of an infectious disease, or the diagnosis of a type of infectious disease.

The terms or elements described in connection with the information providing method may be the same as described in connection with the multi-detection method for microorganisms.

An embodiment of the present disclosure provides a method of increasing the efficiency of a FISH analysis, the method including treating a sample including microorganisms with 20% (v/v) to 25% (v/v) ethanol and treating the sample with 95% (v/v) to 100% (v/v) methanol.

The sample may include microorganisms, for example, gram-positive bacteria such as B. subtilis, or S. aureus, S. epidermidis, and gram-negative bacteria such as E. coli, P. aeruginosa, or S. typhimurium.

The microorganisms may include a bacterium, a virus, a mold, a fungus, or a combination thereof, and may specifically include Gram-positive bacteria. In regard to the detection of microorganisms through conventional FISH analysis, the detection efficiency of Gram-positive bacteria was not good because the fixation and permeabilization of Gram-positive bacteria by known methods were not sufficient. However, according to the method according to one aspect, the effect of fixation and/or permeabilization with respect to all microorganisms including Gram-positive bacteria is excellent.

In regard to the method, the efficiency of FISH analysis may be increased by increasing the degree of fixation and/or permeabilization of the microorganisms.

The "fixation" may refer to fixing the internal and/or external environment of microorganisms in order to bind a probe to the microorganisms. The "permeabilization" may refer to making the microorganisms permeable so that the probe is introduced into the microorganisms. In general, the fixation and/or permeabilization of microorganisms in FISH analysis is performed using about 4% paraformaldehyde, about 50% cold ethanol or about 70% ethanol, etc., which are, however, not enough for the fixation and permeabilization of some gram-negative bacteria or most gram-positive bacteria. However, according to the method according to one aspect, effective fixation and/or permeabilization can be performed on most microorganisms including gram-positive bacteria even without the use of about 4% paraformaldehyde, about 50% cold ethanol or about 70% ethanol, etc., which are used in methods of the related art. Accordingly, the efficiency of FISH analysis may be increased.

The method may include treating the sample containing microorganisms with 20% (v/v) to 25% (v/v) ethanol. The ethanol may have a concentration of about 20% (v/v) to about 25% (v/v), about 20% (v/v) to about 24.5% (v/v), or about 20% (v/v) to about 24% (v/v).

In regard to the method, the sample containing microorganisms may be treated with the ethanol for about 1 minute to 60 minutes, for example, about 2 minutes to about 50 minutes, about 3 minutes to about 40 minutes, about 4 minutes to about 30 minutes, about 5 minutes to about 20 minutes, or for about 10 minutes. When the ethanol is treated for too short a time, fixation or permeabilization of microorganisms may not be sufficient, and when the ethanol is treated for too long, microorganisms may be damaged so that may not be analyzed.

In regard to the method, ethanol may be processed at room temperature, but embodiments are not limited thereto.

The method may include treating the sample with 95% (v/v) to 100% (v/v) methanol. The methanol may have the concentration of about 95% (v/v) to about 100% (v/v), about 96% (v/v) to about 100% (v/v), about 97% (v/v) to about 100% (v/v), about 98% (v/v) to about 100% (v/v), or about 99% (v/v) to about 100% (v/v).

In regard to the method, the sample may be treated with the methanol for about 1 minute to 60 minutes, for example, about 2 minutes to about 50 minutes, about 3 minutes to about 40 minutes, about 4 minutes to about 30 minutes, about 5 minutes to about 20 minutes, or for about 10 minutes. When the methanol is treated for too short a time, fixation or permeabilization of microorganisms may not be sufficient, and when the methanol is treated for too long, microorganisms may be damaged so that may not be analyzed.

In regard to the method, methanol may be processed at room temperature, but embodiments are not limited thereto.

In regards to the method, when the treating with methanol is included after the treating with ethanol, the efficiency of fixation and/or permeabilization of microorganisms is improved, and thus the efficiency of FISH analysis may be improved.

The method may further include treating with 1× phosphate buffered saline (PBS), saline, or 1× tris buffered saline (TBS). The PBS, saline, or TBS is not limited as long as being a solution for removing the methanol treated in the previous step. The treatment with PBS, saline, or TBS may be repeated once or twice or more.

In regard to the method, hybridizing the probe after the fixation and permeabilization of microorganisms may be further included. The hybridizing the probe may be performed by a method known in the art, and may be performed by, for example, treating formamide, a saline sodium citrate (SSC) buffer, or a hybridization solution.

In an embodiment, the hybridization solution may include 15% (v/v) ethylene carbonate, 20% (v/v) dextran sulfate, 600 mM NaCl, and 10 mM citrate, of which concentrations may be appropriately selected by those skilled in the art. The pH of the hybridization solution may be in the range of 6.0 to 6.5, 6.1 to 6.3, or 6.2, and is not limited thereto.

The treating with the formamide or SSC buffer may be performed at room temperature, and is not limited thereto.

The treating with the hybridization solution may be performed at about 20° C. to about 80° C., about 30° C. to about 70° C., about 40° C. to about 60° C., about 40° C. to about 50° C., about 42° C. to about 48° C., about 43° C. to about 47° C., about 44° C. to about 46° C., or about 45° C., and the temperature therefor is not limited thereto.

The probe may be labeled with a detectable labeling material. The labeling material may be a fluorescent material, a chromogenic substance, or a chemiluminescent substance, and by being labeled with the labeling material, microorganisms can be visualized (or imaged) and detected.

In regard to the method, the detecting the signal emitted from the hybridized probe may be performed by a method known in the art, for example, histochemistry, immunohistochemistry, immunofluorescence, color-in-situ hybridization, FISH, and the like.

The terms or elements described in connection with the method of increasing the efficiency of the FISH analysis may be the same as those described in connection with the multi-detection method for microorganisms and the information providing method.

An embodiment of the present disclosure provides a method of evaluating antibiotic susceptibility, the method including calculating the amount of test microorganisms in the first microbial group and the second microbial group, and comparing the calculated amounts of the test microorganisms, wherein the first microbial group is obtained by culturing microorganisms containing the test microorganisms in an antibiotic-added medium, and the second microbial group is obtained by culturing microorganisms containing the test microorganisms in an antibiotic-free medium.

The term "test microorganisms" used herein refers to microorganisms to be tested for sensitivity to antibiotics, and may include a bacterium, a virus, a mold, a fungus, or a combination thereof. The test microorganisms may include gram-negative bacteria or gram-positive bacteria, and may include, for example, *Enterococcus faecium, Staphylococcus aureus, Klebsiella species, Acinetobacter baumannii, Pseudomonas aeruginosa*, or *Enterobacter* species, and the test microorganisms may include any microorganisms capable of acquiring antibiotic resistance.

The term "microbial group" used herein refers to a microbial group in which one or more microorganisms are mixed. The microbial group may be obtained from a sample containing the test microorganisms, and optionally, the microbial group may refer to a microbial group including the test microorganisms and antibiotic-resistant microorganisms.

The term "sample" used herein is a sample containing at least one microorganism, and may be a biological sample, an environmental sample, or a food sample. The biological sample refers to a liquid sample obtained from a living organism, and may be blood, plasma, serum, ascites fluid, bone marrow fluid, lymph fluid, saliva, tear fluid, mucosal fluid, amniotic fluid, urine, sputum, or a combination thereof. The environmental sample may include a water quality sample or a soil sample.

The term "antibiotic susceptibility" used herein refers to the degree to which target microorganisms are killed or inhibited by antibiotics, and microorganisms with low or no antibiotic susceptibility, i.e., antibiotic-resistant microorganisms, are of great public health or clinical importance. The antibiotic may be, for example, one or more selected from the group consisting of amikacin, amoxicillin, ampicillin, aztreonam, benzylpenicillin, clavulanic acid, cefazolin, cefepime, cefotaxime, cefotetan, cefoxitin, cefpodoxime, ceftazidime, ceftriaxone, cefuroxime, ciprofloxacin, dalfopristin, doripenem, daptomycin, ertapenem, erythromycin, gentamicin, imipenem, levofloxacin, linezolid, meropenem, minocycline, moxifloxacin, nitrofurantoin, norfloxacin, piperacillin, quinupristin, rifampicin, streptomycin, sulbactam, sulfamethoxazole, telithromycin, tetracycline, ticarcillin, tigecycline, tobramycin, trimethoprim, and vancomycin, and is not limited thereto.

The term "evaluation" used herein may refer to determining the level of a certain phenomenon. The evaluation in the present disclosure may be determining whether test microorganisms have antibiotic susceptibility and/or the degree of antibiotic susceptibility of test microorganisms, for example, whether or not the test microorganisms are antibiotic-resistant microorganisms.

In one embodiment, the comparing the amount of the calculated test microorganisms may refer to quantitatively comparing the calculated test microorganisms, and in the case where two or more types of microorganisms are present, comparing the ratio of microorganisms.

In an embodiment, the comparing the amounts of the calculated test microorganisms may further include evaluating that when the ratio of test microorganisms in the first microbial group is lower than that of the second microbial group, the test microorganisms have antibiotic susceptibility; or when the ratio of test microorganisms in the first microbial group is equal to or higher than that of the second microbial group, the test microorganisms have antibiotic resistance.

The first microbial group is obtained by culturing microorganisms containing test microorganisms in an antibiotic-added medium, and the second microbial group may be obtained by culturing microorganisms containing test microorganisms in an antibiotic-free medium. In this regard, the second microbial group is cultured in a medium supplemented with buffer in place of the antibiotic, which is added to the first microbial group. For example, the culturing may be performed in a medium including 1×PBS, saline, distilled water, glucose injection, or 1×TBS.

In an embodiment, the first microbial group may be 2 or more, and the 2 or more of the first microbial groups may be obtained by culturing microorganisms containing test microorganisms in each medium in which the concentration of an antibiotic added varies.

The concentration of the antibiotic may be adjusted to increase or decrease sequentially, for example, and quantitative antibiotic susceptibility may be determined through such a change in concentration.

According to an embodiment, by obtaining a first microbial group and a second microbial group according to one aspect from a sample containing test microorganisms (*E. coli* K-12 or ER7) and antibiotic-resistant microorganisms, *E. faecalis*, and measuring the ratio of the test microorganisms in the sample, variables such as the growth rate of each microorganism may be excluded, and as a result, antibiotic sensitivity may be easily determined with only about 1 hour of culturing.

Therefore, the comparing the ratio of test microorganisms in the first microbial group and the second microbial group may enable antibiotic susceptibility to be determined in a short time, in combination with the ratio calculation of microorganisms through image-based analysis, compared to the conventional antibiotic susceptibility evaluation method, which essentially includes a process of identifying microorganisms in a sample and growing the identified microorganisms. In an embodiment, the first microbial group and the second microbial group may be obtained by culturing the microorganisms for about 0.2 hours to 24 hours, and the culturing time may be, for example, about 0.2 hours to about 20 hours, about 0.2 hours to about 15 hours, about 0.2 hours to about 10 hours, about 0.2 hours to about 6 hours, about 0.2 hours to about 4 hours, about 0.2 hours to about 3 hours, about 0.5 hours to about 24 hours, about 0.5 hours to about 20 hours, about 0.5 hours to about 15 hours, about 0.5 hours to about 10 hours, about 0.5 hours to about 8 hours, about 0.5 hours to about 6 hours, about 0.5 hours to about 4 hours, about 0.5 hours to about 3 hours, about 1 hour to about 24 hours, about 1 hour to about 20 hours, about 1 hour to about 15 hours, about 1 hour to about 10 hours, about 1 hour to about 8 hours, about 1 hour to about 6 hours, about 1 hour to about 5 hours, about 1 hour to about 4 hours, about 1 hour to about 3 hours, about 1 hour to about 2 hours, about 2 hours to about 24 hours, about 2 hours to about 20 hours, about 2 hours to about 15 hours, about 2 hours to about 10 hours, about 2 hours to about 8 hours, about 2 hours to about 6 hours, about 2 hours to about 5 hours, about 2 hours to about 4 hours, or about 2 hours to about 3 hours, and may be changed as needed.

In an embodiment, calculating the ratio of the test microorganisms may include quantifying a signal emitted from a probe hybridized with the microorganisms through a probe-based analysis.

The probe may be labeled with a fluorescent material, a chromogenic substance, or a chemiluminescent substance.

The probe-based analysis may include hybridizing a genetic material of microorganisms with a probe and detecting a signal emitted from the hybridized probe. In detail, the presence or absence of microorganisms or the type of microorganisms may be determined by comparing the signal of the part where the signal emitted from the probe hybridized with the microorganisms exists and the signal of the other part. In addition, by comparison using a standard sample containing microorganisms having a known concentration in advance, the concentration of microorganisms included in the sample may be obtained.

The probe-based analysis may be performed by histochemistry, immunohistochemistry, immunofluorescence, chromogenic in situ hybridization, fluorescence in situ hybridization (FISH), etc., for example, Single-molecule RNA FISH, Fiber FISH, Q-FISH, Flow-FISH, MA-FISH, or Hybrid Fusion-FISH.

In an embodiment, the method may further include concentrating a sample containing the test microorganisms.

The term "concentration" used herein may refer to any activity that increases the concentration of microorganisms in a sample. The concentration may refer to enabling detection of microorganisms by separating and concentrating bacteria from a sample.

The concentrating may be performed using known techniques known in the art without limitation, and for example, a sample may be brought into contact with magnetic particles so that microorganisms included in the sample bind to the magnetic particles. (Korean Registered Patent No. 10-2020-0084688).

In an embodiment, the method may further include calculating a ratio of the test microorganisms in each of the second microbial group and in the third microbial group and comparing the calculated ratios of test microorganisms, wherein the third microbial group may be a group that is not cultured and includes test microorganisms.

Comparing the ratio of the test microorganisms in the second microbial group and the third microbial group may correspond to evaluating errors that may occur in the process of culturing the microbial group. For example, when there is little or no variation in the ratio of test microorganisms in the second microbial group and the third microbial group, antibiotic susceptibility-related results based on the ratio of the test microorganisms in the first microbial group and the second microbial group are reliable. On the other hand, when the deviation of the ratio of the test microorganisms in the second microbial group and the third microbial group is large, this indicates that the survival of the test microorganisms varies depending on the culture conditions, which can be interpreted as a lack of confidence in results related to antibiotic susceptibility based on the proportion of test microorganisms in the first microbial group and the second microbial group.

Therefore, the method for evaluating antibiotic susceptibility of test microorganisms in a sample according to one aspect can enable the evaluation of antibiotic susceptibility in a short time without a process such as identifying microorganisms and growing the identified microorganisms. Also, due to a self-validation process, the accuracy of antibiotic susceptibility results may be further improved.

The terms or the elements described herein in connection with the method of evaluating the antibiotic susceptibility are the same as described in the multi-detection method for microorganisms, the information providing method, and the method of increasing the efficiency of the FISH analysis.

An embodiment of the present disclosure provides a method of detecting or identifying microorganisms, the method including: (a) contacting a degradable probe, which is linked to a detection label via a degradable covalent bond, with microorganisms in a sample to perform hybridization with the microorganisms; (b) detecting a signal emitted from the probe hybridized with the microorganisms; (c) separating and removing the detection label linked to the probe hybridized with the microorganisms from the probe; and (d) repeating steps (a) to (c) at least once for the microorganisms from which the detection label linked to the probe hybridized with the microorganisms has been removed.

The method of detecting or identifying microorganisms includes (step (a)) performing hybridization with the microorganisms in the sample by bringing a degradable probe which is linked to a detection label via a degradable covalent bond into contact with the microorganisms in the sample.

The probe may be an antibody, aptamer, DNA, RNA, PNA, oligosaccharide, a peptide, or a protein, and is not limited thereto. In an embodiment, the probe may be accepted without limitation as long as it may bind to a part of a microorganism, for example, a polysaccharide expressed on the surface of a microorganism, a genetic material (DNA, RNA, etc.) in the microorganism, or a protein of the microorganism. In an embodiment, the probe (e.g., structure or sequence of the probe) may be designed to bind specifically to a specific microorganism or microbial species. In an embodiment, the probe may be a PNA.

The term "PNA" used herein refers to an artificially synthesized polymer similar to DNA or RNA. In an embodiment, PNA refers to a case where the sugar-phosphate backbone of DNA is replaced with a peptide conjugate. The PNA may have a neutral structure that does not have the negative charge characteristic of a DNA backbone structure.

According to an embodiment, when a PNA probe is used as a probe, the time required to detect or identify a specific microbial species may be significantly reduced compared to when a conventional DNA probe is used. Specifically, when using conventional DNA probes, hybridization for about 12 hours still results in low detection efficiency, whereas when using PNA probes, hybridization for only about 1 to 10 minutes can result in significantly increased detection efficiency.

This may be because the PNA probe has better species specificity and membrane permeability than conventional DNA probes. Specifically, since the PNA probe penetrates into microorganisms more rapidly than conventional DNA probes and recognizes ribosomal RNA sequences, the time required to detect or identify a specific microbial species may be significantly shortened.

In addition, the PNA probe exhibits various advantages over conventional DNA probes, specifically as follows. First, the PNA probe has strong binding force because it is not charged. DNA probes are electrically negatively charged, so when DNA binds to form a double helix, repulsive forces exist between the same poles. However, since PNA probes have a neutral, uncharged backbone, electrical repulsion does not occur when binding to DNA or RNA. Therefore, the PNA probe may bind to the target gene more strongly than the DNA probe. Second, PNA probes have high stability. Since PNA whose backbone is substituted with a peptide conjugate is chemically closer to a peptide than a nucleic acid, it may maintain the performance thereof with strong resistance to nucleases and the like. Thirdly, artificially synthesized PNA probes have the benefit of easy secondary modification to utilize detection labels or useful molecules. By connecting specific molecules or functional groups to the chemical structure of PNA, the physicochemical properties thereof may be modifiable according to the purpose.

According to an embodiment, the probe may include: a PNA probe having the sequence of SEQ ID NO: 1, and used to detect or identify *Escherichia coli, Escherichia dysenteriae, Escherichia flexneri*, or *Escherichia marmotae;* a PNA probe having the sequence of SEQ ID NO: 2, SEQ ID NO: 3, or SEQ ID NO: 4 and used to detect or identify *Klebsiella pneumoniae, Klebsiella quasipneumoniae, Klebsiella variicola, Raoultella ornithinolytica*, or *Raoultella planticola;* a PNA probe having the sequence of SEQ ID NO: 5 or SEQ ID NO: 6 and used to detect or identify *Cronobacter sakazakii, Klebsiella aerogenes, Klebsiella pneumoniae, Klebsiella quasipneumoniae, Klebsiella variicola, Raoultella ornithinolytica*, or *Raoultella planticola;* a PNA probe having the sequence of SEQ ID NO: 7 and used to detect or identify *Cronobacter sakazakii, Edwardsiella piscicida, Klebsiella aerogenes, Klebsiella pneumoniae, Klebsiella quasipneumoniae, Klebsiella variicola, Raoultella ornithinolytica*, or *Raoultella planticola;* a PNA probe having the sequence of SEQ ID NO: 8 and used to detect or identify *Staphylococcus argenteus*, or *Staphylococcus aureus;* a PNA probe having the sequence of SEQ ID 9 and used to detect or identify *Staphylococcus argenteus;* a PNA probe having the sequence of SEQ ID NO: 10 or SEQ ID NO: 11 and used to detect or identify *Pseudomonas aeruginosa;* a PNA probe having the sequence of SEQ ID NO: 12, SEQ ID NO: 13, or SEQ ID NO: 14 and used to detect or identify *Enterococcus faecalis;* a PNA probe having the sequence of SEQ ID NO: 15 and used to detect or identify *Proteus mirabilis;* a PNA probe having the sequence of SEQ ID NO: 16 or SEQ ID NO: 17 and used to detect or identify *Streptococcus pneumoniae;* a PNA probe having the sequence of SEQ ID NO: 18 and used to detect or identify *Enterococcus faecium;* a PNA probe having the sequence of SEQ ID NO: 19 or SEQ ID NO: 20 and used to detect or identify *Streptococcus pyogenes;* a PNA probe having the sequence of SEQ ID NO: 21 or SEQ ID NO: 22 and used to detect or *Streptococcus thermophilus;* a PNA probe having the sequence of SEQ ID NO: 23 or SEQ ID NO: 24 and used to detect or identify *Streptococcus mutans;* a PNA probe having the sequence of SEQ ID NO: 25 and used to detect or identify *Salmonella enterica*; or a combination thereof, and is not limited thereto.

The probe may be linked to a detection label.

The detection label may be selected from the group consisting of enzymes, fluorescent materials, ligands, luminescent substances, microparticles, and radioactive isotopes. In an embodiment, examples enzymes used as the detection label are acetylcholinesterase, alkaline phosphatase, β-D-galactosidase, horseradish peroxidase, and β-latamase, etc., examples of fluorescent materials are fluorescein, Eu3⁺, Eu3⁺ chelate, cryptate, FITC, RITC, FAM, VIC, HEX, Cy5, Cy3, SYBR Green, DAPI, TAMRA, rhodamine, Fluoredite, FluorePrime, ROX, etc., examples of ligands are biotin derivatives and the like, examples of luminescent substances are acridinium esters and isoluminol derivatives, and examples of microparticles are colloidal gold and colored latex, examples of radioactive isotopes are $^{57}$Co, $^{3}$H, $^{125}$I, and $^{125}$I-Bolton Hunter reagent, etc., and are not limited to.

By connecting the probe to the detection label, microorganisms may be visualized (or imaged), and microorganisms may be detected or identified. In the case where a probe linked to the detection label is used, due to the variation of the signal of each detection label, hybridization between the probe and microorganisms and dissociation between the detection label and the probe hybridized with microorganisms may be easily confirmed only by simple imaging.

The probe may be a degradable probe. The "degradable probe" may refer to a probe-detection label complex in which a detection label is linked to a probe via a degradable bond so that the detection label linked to the probe may be easily separated or dissociated from the probe as needed. Therefore, the degradable probe may be easily degraded into a probe and a detection label from the probe-detection label complex as needed.

In an embodiment, the probe may be linked to the detection label through a degradable covalent bond. In addition, the degradable covalent bond may be decomposed or cut by a chemical action. That is, by decomposition or cleavage of the degradable covalent bond by a chemical action, the detection label may be easily separated or dissociated from the probe linked to the detection label via a degradable covalent bond, if necessary. As such, the probe may have degradability characteristics.

The degradable covalent bond may be selected from the group consisting of a disulfide bond, an acid degradable bond, an ester bond, an anhydride bond, a biodegradable bond, and an enzyme degradable bond, and is not limited thereto. In an embodiment, the degradable covalent bond may be a bond that easily undergoes hydrolytic, oxidative, or reductive decomposition.

The chemical action may include all chemical reactions capable of decomposing or cutting the degradable covalent bond. In an embodiment, the chemical action may include hydrolysis, enzymatic degradation, oxidation, and reduction reactions, etc.

In an embodiment, the degradable covalent bond may be a disulfide bond. In an embodiment, the probe may be linked to the detection label by a disulfide bond. In an embodiment, the disulfide bond may be easily decomposed or cut as needed by a chemical action, and thus, the detection label may be easily separated or dissociated from the probe to which the detection label is connected, as needed. The "disulfide bond" refers to a covalent bond between sulfur elements in the form of —S—S— formed by oxidation of two SH groups.

In an embodiment, the chemical action capable of decomposing or cutting the disulfide bond may include a reduction reaction. That is, the disulfide bond may be decomposed or cleaved by a reduction reaction in which —S—S— is replaced with two SH groups by a reducing agent. The reducing agent may be selected from the group consisting of mercaptoethanol, glutathione (GSH), dithiothreitol (DTT), tris(2-carboxyethyl)phosphine (TCEP), cysteine, tris(3-hydroxypropyl)phosphine (THPP), and a combination thereof.

The method may use two or more types of probes. Target sequences the two or more probes bind may be different from each other. In general, genetic mutations that determine the species of microorganisms are scattered rather than concentrated in a specific region of a chromosome, so multiple short probes may be more effective in detecting variation of species than one long probe. In addition, when a long probe is used, a large cost may be incurred in manufacturing the probe, and membrane permeability may be reduced. Therefore, the method may maximize the efficiency of detecting microorganisms by using two or more types of probes having relatively short lengths (e.g., about 10 nt to about 30 nt) and different target regions.

The two or more probes may hybridize to specifically microorganisms of different species or hybridize to specifically microorganisms of the same species. In an embodiment, the two or more types of probes may be capable of hybridizing specifically to two or more different types of microorganisms in a sample, respectively. In addition, the two or more types of probes may be capable of hybridizing specifically to different regions within the same type of microorganism in the sample, respectively. In addition, the two or more types of probes may be the same probe capable of repeatedly hybridizing with the same type of microorganisms in the sample, or the same probe capable of hybridizing to the same region in two or more different types of microorganisms in the sample.

The two or more types of probes may be labeled with the same label, or labeled with different labels, respectively. In an embodiment, the two or more types of probes may be linked to detection labels emitting signals of different colors, respectively.

The method may use the two or more types of probes simultaneously or sequentially. In an embodiment, in the analysis of one cycle including the steps (a) to (c), the two or more types of probes may be simultaneously administered in the step (a) to hybridize with microorganisms in the sample. In addition, in a multiple analysis in which the cycle including the steps (a) to (c) is repeated, a specific type of probe is administered in step (a) of each cycle, so that in each cycle, a different type of probe may be sequentially hybridized to the microorganisms in the sample.

Accordingly, in the method, when the two or more probes specifically hybridize with different types of microorganisms, two or more types of microorganisms from among the microorganisms in the sample may be distinguished from each other. In addition, in the method, when the two or more types of probes respectively hybridize specifically to different regions in the same type of microorganisms, one type of microorganisms from among the microorganisms in the sample may be more accurately distinguished.

Accordingly, the method may be for distinguishing one or more types of microorganisms from among the microorganisms in the sample.

The step (a) of the method may include bringing the probe into contact with microorganisms in the sample to hybridize the same with the microorganisms.

The sample may include a biological sample, an environmental sample, or a food sample. The biological sample may refer to a sample obtained from a biological subject, including a sample derived from a biological tissue or body fluid obtained in vivo or in vitro. In an embodiment, the biological sample may be a bodily fluid (e.g., blood, plasma, serum, saliva, sputum, or urine), organs, tissues, fractions, or cells isolated from mammals, including humans, and is not limited thereto. The sample may also include extracts from biological samples, such as antibodies, proteins, and the like from biological fluids (e.g., blood or urine). The environmental sample may include a water quality sample or a soil sample. The sample may contain microorganisms.

The microorganisms may include a bacterium, a virus, a mold, a fungus, or a combination thereof.

The "hybridization" may refer to a case where the probe binds to a part of a microorganism, for example, a polysaccharide expressed on the surface of the microorganism, a genetic material (DNA, RNA, etc.) in the microorganism, or a protein of the microorganism. In an embodiment, the probe may hybridize with the microorganisms by complementarily binding to a specific nucleotide sequence of a genetic material (DNA, RNA, etc.) in the microorganism. Specific methods, conditions, and reagents for the hybridization are not particularly limited, and may be appropriately selected by a person skilled in the art based on facts known in the art.

According to an embodiment, in regard to the method, when the PNA probe is used, the hybridization takes about 1 to 10 minutes, about 1 minute to about 9 minutes, about 1 minute to about 8 minutes, about 1 minute to about 7 minutes, about 1 minute to about 6 minutes, about 1 minute to about 5 minutes, about 1 minute to about 4 minutes, about 1 minute to about 3 minutes, or about 1 minute to about 2 minutes. In an embodiment, the hybridization may be performed for about 5 minutes or less. As described above, in regard to the method, when the PNA probe is used, since the hybridization time may be significantly shortened, the hybridization may be sufficiently performed only for about 5 minutes or less.

The method of detecting or identifying microorganisms includes detecting a signal emitted from a probe hybridized with the microorganisms (the step (b)).

The detecting may be performed by a method known in the art, for example, histochemistry, immunohistochemistry, immunofluorescence, color in situ hybridization, fluorescence in situ hybridization (FISH), and the like.

The method of detecting or identifying microorganisms includes separating and removing a detection label linked to a probe hybridized with the microorganisms from the probe (the step (c)).

In the removing, with respect to the probe hybridized with the microorganisms, without the need to undergo a non-hybridization of separating the probe from the microorganisms, only the detection label linked to the probe can be separated and removed from the probe hybridized with the microorganisms. In an embodiment, as described above, since the probe hybridized with the microorganisms is a degradable probe linked to the detection label by a degradable covalent bond, the detection label may be very quickly and easily separated and removed from the probe, only by decomposition or cutting of the degradable covalent bond by the chemical action. This makes it very quick and simple to remove already detected signals from a sample for which signal detection has been completed.

According to an embodiment, in the method, in the case where the microorganisms in the sample are hybridized with a degradable probe that is connected to the detection label (e.g., fluorescent material) by a degradable covalent bond, the detection label can be separated from the probe that has hybridized with the microorganisms within about one minute to very quickly remove the already detected signal, without the need to go through a process of separating and removing the probe that has hybridized with the target species from the sample in which the signal has been detected (e.g., washing with an organic solvent). The process of separation and removal of the detection label can be accomplished very simply and rapidly by inducing a chemical reaction (e.g., treatment with a reducing agent) that can decompose or cut the degradable covalent bonds linking the probe hybridized with the target species to the detection label, on the sample in which the signal has been detected. In addition, according to an embodiment, compared to the conventional FISH analysis method in which photobleaching is performed by irradiating a strong laser to remove a fluorescence signal, when the decomposable probe is used, the signal detected may be removed at a significantly increased rate. In addition, in the case where the degradable probe is used, since there is no need to perform strong laser irradiation to remove the detected signal, damage to the sample can be fundamentally prevented.

According to an embodiment, in the method, when using the degradable probe which is linked to a detection label via a degradable covalent bond, the separating and removing the detection label from the probe hybridized with the microorganisms (the step (c)), may be performed for about 5 seconds to about 60 seconds, about 5 seconds to about 50 seconds, about 5 seconds to about 40 seconds, about 5 seconds to about 30 seconds, about 5 seconds to about 20 seconds, or about 5 seconds to about 10 seconds. As described above, in the method, in the case of using a degradable probe linked to the detection label by a degradable covalent bond, since the detection label can be separated and removed very easily and quickly in the step (c), the time of about 1 minute or less is sufficient for the separating and removing of the detection label.

In regard to the method, in order to perform multiple analyzes in which the steps (a) to (c) are repeated, it is very important to quickly remove a previously detected signal from a sample for which signal detection has been completed. Therefore, the process of hybridizing with microorganisms by re-administering a probe connected to a new detection label to the sample for which signal detection has been completed and detecting the signal of the new detection label may be quickly repeated, significantly increasing the analysis efficiency of the multiplex analysis.

Therefore, compared to the conventional FISH analysis method, the method of detecting or identifying microorganisms using the degradable probe can significantly shorten the analysis time by removing the already detected signal more quickly, thereby increasing the analysis efficiency of multiple analysis. In other words, since the method may significantly shorten the analysis time of multiple analysis compared to the conventional FISH analysis method, one or more types of microorganisms may be detected or identified more quickly and accurately from a sample in which multiple types of microorganisms are mixed.

The method of detecting or identifying microorganisms includes repeating the steps (a) to (c) at least once for the microorganisms from which the detection label, linked to the probe hybridized with the microorganisms in the step (c), has been removed (the step (d)).

That is, the method may be performed using a multiple analysis in which the steps (a) to (c) are repeated. In an embodiment, the method may be a method of detecting or identifying microorganisms using a multi-FISH analysis method based on a degradable probe.

The "multiple FISH analysis" may refer to that a plurality of FISH analyses are performed in combination. In an embodiment, FISH analysis of one cycle is followed by FISH analysis of the next cycle sequentially, which may refer to that the FISH analysis is repeated. In addition, the multiple FISH analysis may refer to a FISH analysis using multiple probes or detecting or detecting a plurality of targets.

In an embodiment, the FISH analysis may refer to that the cycle including the steps (a) to (c) is performed once in the method of detecting or identifying microorganisms. In an embodiment, the multiple FISH analysis may refer to that a cycle including the steps (a) to (c) is performed several times in the method of detecting or identifying microorganisms.

In an embodiment, the method of detecting or identifying microorganisms uses the same type of probe for each cycle including the steps (a) to (c), or different types of probes for each cycle including the steps (a) to (c).

In the case where sequences of microorganism species are very similar even if they are not identical, one species of a probe is not enough to accurately detect or identify microorganisms of only a single species. For example, when *E. coli* and *S. enterica* each include very similar sequences that are either identical to the sequence targeted by a particular probe or differ by about 1 bp or more, it is likely that a single FISH analysis with the particular probe could not clearly distinguish between the two species. In addition, one of the problems of the FISH analysis method of detecting or identifying a single species of microorganisms based on imaging is that background signals, noise, and non-target microorganisms may be mistakenly recognized as target microorganisms.

Therefore, according to an embodiment, in regard to the method, when performing the multiple FISH analysis by sequentially using two or more types of probes that specifically respectively target two or more specific regions included in a single species of microorganisms, the match of the detected microbial species can be reconfirmed at each cycle of the multiple FISH analysis. Through this, only a single species of microorganisms may be accurately detected or identified in a sample in which several species of microorganisms are mixed, and the detection error probability may be significantly reduced. In addition, according to an embodiment, in regard to the method, when the multiple FISH analysis is performed using the degradable PNA probe, the hybridization time of the probe with microorganisms may be significantly reduced, as well as the detection label associated with the hybridized probe may be quickly removed, thereby significantly reducing the time required to repeat the process of detecting the signal of a new probe.

Therefore, in regard to the method, when the multiple FISH analysis is performed by sequentially using two or more of degradable probes to detect a single species of microorganisms, the analysis time can be significantly shortened compared to the conventional FISH analysis method while exhibiting significantly better analysis accuracy, thereby significantly increasing the analysis efficiency.

Since the number of fluorescence signal colors that may be distinguished by fluorescence imaging is limited, in order to detect or identify two or more microbial species through multiple FISH analysis, the fluorescence signal used to detect a specific microbial species needs to be removed and, to detect other microorganisms, it is necessary to reuse the fluorescence signal of the same color. In this case, it is very important to quickly remove the fluorescence signal that has been detected. In the case of existing FISH-based microorganisms identification technology, in order to sequentially detect or identify two or more species of microorganisms in a single sample, a time-consuming process is required to remove the probe-fluorescent material complex that has hybridized with the microorganisms after detection, followed by a de-hybridization process in which a new probe-fluorescent material complex is administered to re-hybridize with the microorganisms. For example, in the case of the existing DNA probe-based FISH analysis method, about 1 hour is required for probe hybridization and non-hybridization per cycle. In addition, in regard to the existing FISH-based microorganisms identification technology, when detecting or identifying two or more microorganisms, a slide channel for each species needs to be separately prepared in order to shorten the analysis time, and in this case, the detection efficiency is bound to decrease with the diversity of targeted species.

On the other hand, according to an embodiment, in order to detect a plurality of microorganisms of two or more species, in regard to the method, when the multiple FISH analysis is performed using the two or more degradable probes sequentially, after detection of a specific microbial species by the first cycle, only the detection label can be rapidly removed from the probe hybridized to the microbe without the need for a de-hybridization process to remove the probe-detection label complex hybridized to the microbe. Accordingly, a second cycle process of detecting a signal of a new probe targeting a microbial species different from the microbial species detected in the first cycle may be quickly repeated. In addition, according to an embodiment, in regard to the method, when the multiple FISH analysis is performed using the two or more degradable probes sequentially, each cycle of FISH analysis with a different target species can be repeated very rapidly, as described above, to rapidly detect each of the two or more plurality of microorganism species sequentially within a single slide sample. This eliminates the challenges of traditional FISH analysis and maximizes detection efficiency for targeted microorganisms in samples.

Therefore, in regard to the method, in order to detect a plurality of two or more microbial species, when performing the multiple FISH analysis by sequentially using two or more kinds of the degradable probes, the analysis time can be significantly shortened compared to the conventional FISH analysis while exhibiting significantly better analysis accuracy, thereby significantly increasing the analysis efficiency. This allows for faster, more accurate detection or identification of two or more microbial species within a single sample.

The method of detecting or identifying microorganisms may further include concentrating and fixing the microorganisms performed before the step (a) and permeabilizing the microorganisms.

Specific methods, conditions, and reagents used in the concentrating and fixing the microorganisms are not particularly limited, and may be appropriately selected by a person skilled in the art based on facts known in the art. By concentrating and fixing the microorganisms, in regard to the method, a probe not bound to the microorganisms and a detection label separated from the probe may be removed, and a new probe may be administered to contact the microorganisms again. Therefore, by concentrating and fixing the microorganisms in this step, the probe may be sequentially hybridized with the microorganisms, and thus, multiple detection of the microorganisms may be performed. The "fixing" may refer to attaching or fixing microorganisms to or on a specific location or region.

In an embodiment, magnetic particles may be used in the concentrating and fixing the microorganisms. In an embodiment, by contacting the sample and the magnetic particles, microorganisms included in the sample may bind to the magnetic particles. By applying a magnetic field to a sample including the microorganisms bonded with the magnetic particles, only the microorganisms bonded to the magnetic particles can be concentrated and fixed in a specific region. The magnetic field may be formed in any conventional way. For example, the formation of the magnetic field may be performed using a magnet such as an electromagnet or a permanent magnet by electromagnetic induction. The magnetic particles may be manufactured through known methods or commercially sold.

In an embodiment, the concentrating and fixing the microorganisms may use a centrifugation method. Further, in an embodiment, the concentrating and fixing the microorganisms includes coating the surface of the slide with a material capable of attaching the microorganisms (for example, a cationic material) and attaching the microorganisms in the sample on the surface of the slide. A material capable of attaching the microorganisms may be poly-l-lysine, but is not limited thereto.

In an embodiment, the concentrating and fixing the microorganisms may further include performing fixation of the microorganisms by the treatment using a fixative. The "fixation" may refer to fixing the internal and/or external environment of microorganisms in order to bind a probe to the microorganisms. The fixative (fixative solution) may be about 2% to about 5% formaldehyde solution, about 20% to about 60% ethanol solution, about 90% or more methanol solution, or a combination thereof, and is not limited thereto.

Specific methods, conditions, and reagents used in the permeabilizing the microorganisms are not particularly limited, and may be appropriately selected by a person skilled in the art based on facts known in the art. The "permeabilization" may refer to making microorganisms permeable so that the probe is introduced into the microorganisms.

In an embodiment, in the permeabilizing the microorganisms, the permeabilization treatment may be performed on the fixed microorganisms (or the microorganisms that have undergone the fixation) for about 10 minutes to about 40 minutes with a cell permeability reagent. In addition, reagents necessary for FISH analysis, such as FISH buffer, DAPI, and 2×SSC buffer, may be additionally used. The cell permeability reagent may be about 1 mg/mL to about 10 mg/mL lysozyme solution, about 20% to about 80% ethanol solution, about 90% to about 100% methanol solution, or a combination thereof, and is not limited thereto.

The method may be performed using a microfluidic device. The microfluidic device may be referred to as a microfluidic channel, a microfluidic pipe, a microfluidic tube, and the like.

In an embodiment, the method may include: (i) injecting a sample and magnetic particles into a microfluidic device to combine microorganisms in the sample and magnetic particles in a microfluidic device, or injecting a combination of microorganisms in the sample and magnetic particles into a microfluidic device; (ii) applying a magnetic field to a specific region within the microfluidic device, concentrating only the microorganisms combined with the magnetic particles, and fixing the concentrated microorganisms to the specific region within the microfluidic device; (iii) injecting a degradable probe, which is linked to a detection label via a degradable covalent bond, into the microfluidic device and bringing the degradable probe into contact with the fixed microorganisms to hybridize with the microorganisms; (iv) detecting a signal emitted from the probe hybridized with the microorganisms by a device connected to the microfluidic device; (v) injecting a substance that can decompose or cut the degradable covalent bond into the microfluidic device, separating and removing, from the probe, the detection label connected to the probe hybridized with the microorganisms; and (vi) repeating the steps (iii) to (v) at least once for the microorganisms fixed to the specific region in the microfluidic device from which the detection label linked to the probe hybridized with the microorganisms has been removed.

The method may further include determining the presence or absence of microorganisms or the type of microorganisms by using information about a probe from which a signal is emitted.

The terms or elements described in the method of detecting or identifying microorganisms are the same as described in connection with the multi-detection method for microorganisms, the information providing method, the method of increasing the efficiency of FISH analysis, and the method of evaluating antibiotic susceptibility.

An embodiment of the present disclosure provides a method of providing information on the diagnosis of infectious diseases, the method including: (a) contacting a degradable probe which is linked to a detection label via a degradable covalent bond with microorganisms in a sample to perform hybridization with the microorganisms; (b) detecting a signal emitted from the probe hybridized with the microorganisms; (c) separating and removing the detection label linked to the probe hybridized with the microorganisms from the probe; and (d) repeating the steps (a) to (c) at least once for the microorganisms from which the detection label linked to the probe hybridized with the microorganisms has been removed.

The information providing method may include determining the presence or absence of microorganisms or the type of microorganisms by using information about a probe from which a signal is emitted. By determining the type of microorganisms included in the sample, it is possible to provide information about the likelihood of developing an infectious disease, the onset of an infectious disease, or the diagnosis of a type of infectious disease.

The terms or elements described in the information providing method are the same as described in connection with the multi-detection method for microorganisms, the information providing method, the method of increasing the efficiency of FISH analysis, the method of evaluating antibiotic susceptibility, and the method of detecting or identifying microorganisms.

An embodiment of the present disclosure provides a composition for detecting or identifying microorganisms, the composition including a degradable probe which is linked to a detection label via a degradable covalent bond.

According to an embodiment, the probe may include: a PNA probe having the sequence of SEQ ID NO: 1, and used to detect or identify *Escherichia coli, Escherichia dysenteriae, Escherichia flexneri,* or *Escherichia marmotae;* a PNA probe having the sequence of SEQ ID NO: 2, SEQ ID NO: 3, or SEQ ID NO: 4 and used to detect or identify *Klebsiella pneumoniae, Klebsiella quasipneumoniae, Klebsiella variicola, Raoultella ornithinolytica,* or *Raoultella planticola;* a PNA probe having the sequence of SEQ ID NO: 5 or SEQ ID NO: 6 and used to detect or identify *Cronobacter sakazakii, Klebsiella aerogenes, Klebsiella pneumoniae, Klebsiella quasipneumoniae, Klebsiella variicola, Raoultella ornithinolytica,* or *Raoultella planticola;* a PNA probe having the sequence of SEQ ID NO: 7 and used to detect or identify *Cronobacter sakazakii, Edwardsiella piscicida, Klebsiella aerogenes, Klebsiella pneumoniae, Klebsiella quasipneumoniae, Klebsiella variicola, Raoultella ornithinolytica,* or *Raoultella* planticola;

a PNA probe having the sequence of SEQ ID NO: 8 and used to detect or identify *Staphylococcus argenteus,* or *Staphylococcus aureus;* a PNA probe having the sequence of SEQ ID 9 and used to detect or identify *Staphylococcus argenteus;* a PNA probe having the sequence of SEQ ID NO: 10 or SEQ ID NO: 11 and used to detect or identify *Pseudomonas aeruginosa;* a PNA probe having the sequence of SEQ ID NO: 12, SEQ ID NO: 13, or SEQ ID NO: 14 and used to detect or identify *Enterococcus faecalis;* a PNA probe having the sequence of SEQ ID NO: 15 and used to detect or identify *Proteus mirabilis;* a PNA probe having the sequence of SEQ ID NO: 16 or SEQ ID NO: 17 and used to detect or identify *Streptococcus pneumoniae;* a PNA probe having the sequence of SEQ ID NO: 18 and used to detect or identify *Enterococcus faecium;* a PNA probe having the sequence of SEQ ID NO: 19 or SEQ ID NO: 20 and used to detect or identify *Streptococcus pyogenes;* a PNA probe having the sequence of SEQ ID NO: 21 or SEQ ID NO: 22 and used to detect or *Streptococcus thermophilus;* a PNA probe having the sequence of SEQ ID NO: 23 or SEQ ID NO: 24 and used to detect or identify *Streptococcus mutans;* a PNA probe having the sequence of SEQ ID NO: 25 and used to detect or identify *Salmonella enterica;* or a combination thereof, and is not limited thereto.

The terms or elements described in connection with the composition are the same as described in connection with the multi-detection method for microorganisms, the information providing method, the method of increasing the efficiency of FISH analysis, the method of evaluating antibiotic susceptibility, and the method of detecting or identifying microorganisms.

Advantageous Effects of Disclosure

According to one aspect of the method, microorganisms can be detected without culturing the microorganisms, or purifying or amplifying their genetic material, by concentrating the microorganisms in a sample. In addition, microorganisms included in the sample can be fixed and repeatedly detected by washing, allowing for multiple detections using different probes.

According to a method according to one aspect, the efficiency of fixation and/or permeabilization of microorganisms in the sample is be improved, thereby enabling efficient analysis of most microorganisms, including gram-positive bacteria that are difficult to be analyzed by FISH analysis when methods of the related art are used.

According to a method according to one aspect, antibiotic susceptibility in a sample can be evaluated within several hours by quantifying and analyzing the level of test microorganisms, for example, the ratio of test microorganisms in a sample through a probe-based analysis method.

According to a method or a composition according to one aspect, since the probe capable of hybridizing with microorganisms in the sample is connected to the detection label by a degradable covalent bond, after the detection of the signal emitted from the probe hybridized with microorganisms is completed, the probe from the probe Detection labels can be separated and removed very easily and quickly. Therefore, the process of hybridizing with microorganisms by re-administering a probe linked to a new detection label into the sample and detecting a signal of the new detection label can be quickly repeated. This can significantly increase the efficiency of multiple analyses to sequentially detect multiple species of microorganisms, or to reconfirm detection results for a single species of microorganisms. Thus, according to the methods or compositions according to one aspect, the problems of FISH analysis of the related art including long analysis time, decreased analysis accuracy, and decreased analysis efficiency can be solved, and one or more microorganisms can be detected or identified from a sample containing a mixture of multiple species of microorganisms very quickly and accurately.

BRIEF DESCRIPTION OF DRAWINGS

FIG. 4 shows fluorescence micrographs of primary FISH results for *S. aureus* (A), results of washing with formamide solution (B), and secondary FISH results for *S. aureus* (C).

MODE OF DISCLOSURE

Hereinafter, the present disclosure will be described in more detail through examples. However, these examples are intended to illustrate the present disclosure by way of example, and the scope of the present disclosure is not limited to these examples.

I. Multiple Detection of Microorganisms Through FISH Analysis Using Magnetic Particles Example 1. Sample Preparation 1.1. Sample Processing Magnetic nanoparticles were used to concentrate and fix a sample. In an embodiment, lectin (10405-HNAS, Human Mannose Binding Lectin, Sinobio, China), which is a microorganism attachment protein, was coated on the surface of magnetic nanoparticles (200 nm, Ademtec, France). The magnetic nanoparticles coated with lectin were mixed with TBST buffer (including 5 mM $CaCl_2$)) containing microorganisms (*E. coli* or *S. aureus*). The microorganisms are attached to the magnetic nanoparticles by the lectin coated on the surface of the magnetic nanoparticles, and by the mixed magnetic nanoparticles, the magnetic susceptibility of the entire sample is changed. Samples were treated and prepared in the same way.

1.2. Concentrating of Pathogenic Microorganisms in Samples Using Magnetic Particles In order to concentrate pathogenic microorganisms present in the sample, first, 99.9% ethanol, distilled water, and 1× phosphate buffered saline (PBS) were sequentially flowed into an inlet of a microfluidic channel using a syringe pump or a pneumatic pump to wash the microfluidic channel. The microfluidic channel used was fabricated by photolithography and PDMS micromolding. After washing the microfluidic channel, the sample treated according to Example 1.1. was flowed through the microfluidic channel while simultaneously forming a magnetic field using a permanent magnet or an electromagnet. When a magnetic field is formed around the microfluidic channel, the magnetic nanoparticles mixed in the sample are gathered around the magnetic field. In this regard, magnetic nanoparticles captured around the magnetic field are in a state of bound to pathogenic microorganisms in the sample by lectins linked to the surface of the magnetic nanoparticles.

Therefore, when the sample is flown through the microfluidic channel, the magnetic nanoparticles combined with the microorganisms in the sample are attached around the magnetic field and only the sample flows, so that the microorganisms are concentrated.

Figure 1:
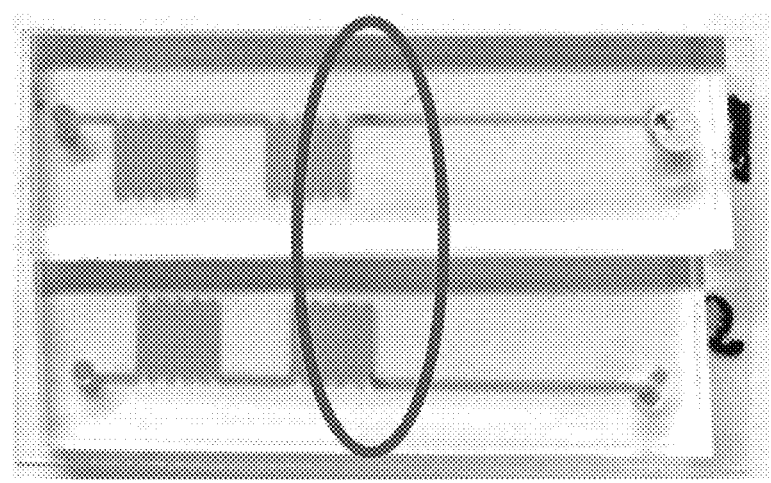
FIG. 1 shows an image of microorganisms concentrated in a channel, the microorganisms binding to magnetic nanoparticles in a channel by forming a magnetic field in a microfluidic channel.

FIG. 1 shows the image of microorganisms concentrated in a channel, the microorganisms binding to magnetic nanoparticles in a channel by forming a magnetic field in a microfluidic channel.

Example 2. Detection of Microorganisms Through FISH Analysis 2.1. FISH Analysis Method Fluorescence in situ hybridization (FISH) analysis was performed to detect the microorganisms concentrated in Example 1. Cell permeability reagent, FISH buffer, DAPI, and 2×SSC buffer, which are reagents necessary for FISH analysis, were sequentially flowed through a microfluidic channel in which microorganisms were concentrated to perform FISH analysis on the captured microorganisms. After all treatments, image analysis was performed via fluorescence microscopy.

2.2. Identification of Microorganisms Through Microorganism-Specific Probe Staining Microorganisms attached to and captured by magnetic nanoparticles are attached to magnetic nanoparticles through lectin, which is an immunoprotein that recognizes various polysaccharides expressed on the surface of microorganisms. Accordingly, the microorganisms may have various types of microorganisms. In order to identify various types of microorganisms, staining was performed with a microorganism-specific probe as follows.

2.2.1. *E. coli* Detection

FISH was performed in the same manner as in Example 2.1 using a common probe labeled with Cy3 (SEQ ID NO: 26: GGTGTGACGGGCGGTGTGTACAAG) and an *E. coli* 16s rRNA specific probe labeled with Cy5 (SEQ ID NO: 27: GGTAAGCGCCCTCCCGAAGGTTAAGCTACC).
Results were confirmed using an epi-fluorescence microscope under conditions of light source: 130 W Xenon lamp, acquisition condition: 20% power, and CCD exposure time: 100 ms.

Figure 2:
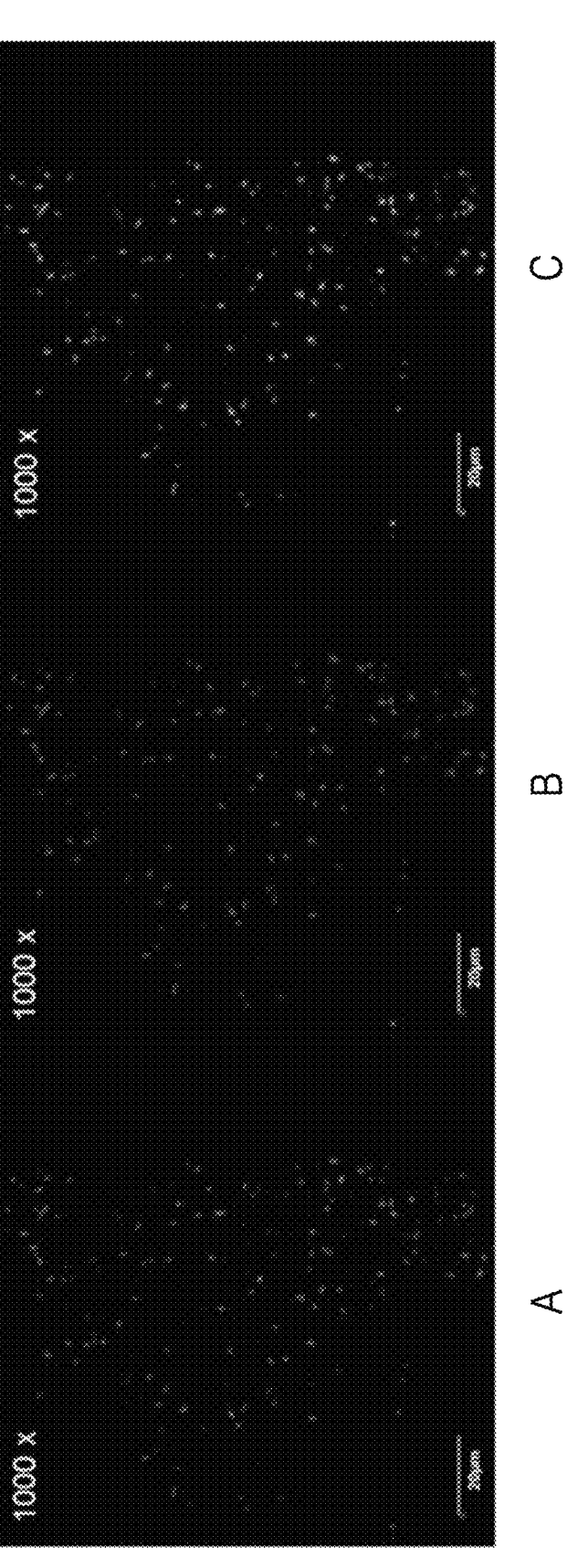
FIG. 2 shows detection results of *E. coli* obtained by fluorescence in situ hybridization (FISH) analysis using magnetic particles.

FIG. 2 shows detection results of *E. coli* obtained by FISH analysis using magnetic particles. A of FIG. 2 shows a photomicrograph confirming the results of FISH analysis using a common probe labeled with Cy3. B of FIG. 2 shows a photomicrograph confirming the results of FISH analysis using an *E. coli* 16s rRNA-specific probe labeled with Cy5. C of FIG. 2 shows a merge of images of A and B of FIG. 2.

As a result, it can be seen that, as shown in FIG. 2, by concentrating the microorganisms, various microorganisms present in the sample were detected without a process of purifying, culturing, or amplifying the nucleic acid, and from among the microorganisms, *E. coli* could be specifically detected.

2.2.2. *S. aureus* Detection

In the same sample in which *E. coli* was detected, FISH analysis was performed in the same way as in 2.2.1. to detect *S. aureus*, except that the probe used was a common probe labeled with Cy3 and a Cy5-labeled *S. aureus* 16s. rRNA specific probe (SEQ ID NO: 28: GGGAT-TTGCTTGACCTCGCGGTTTCGCTGCCC).

Figure 3:
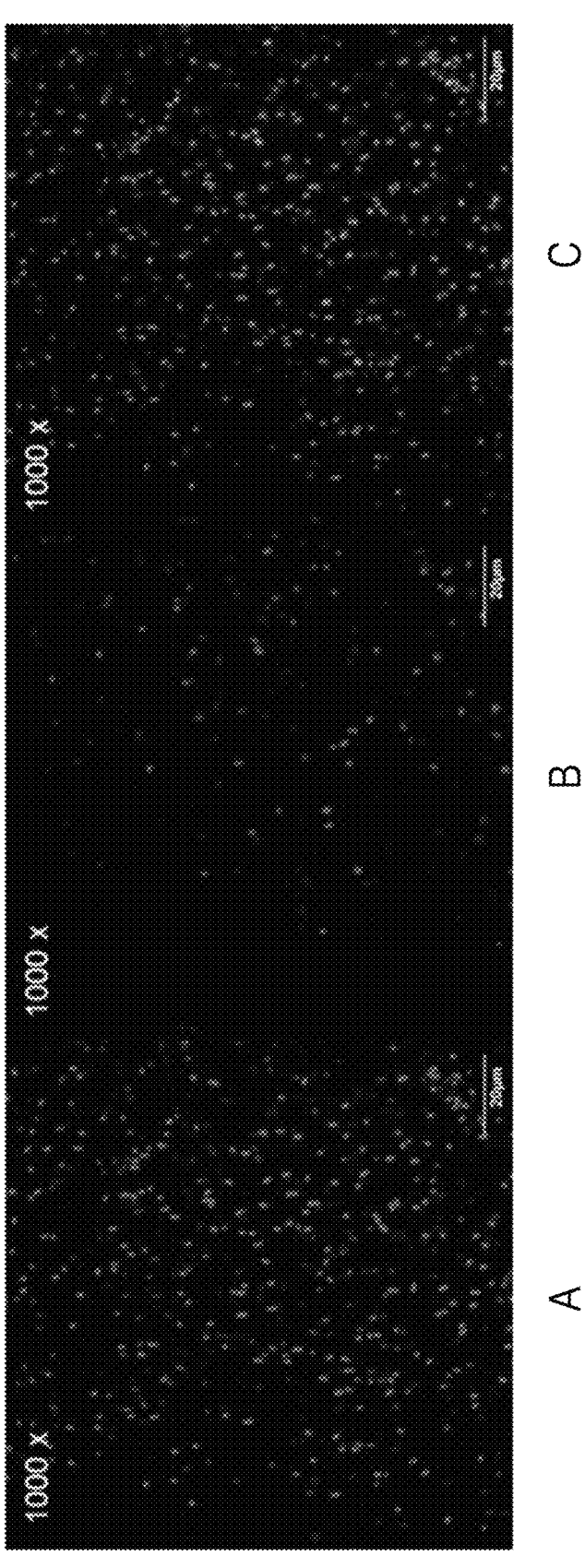
FIG. 3 shows detection results of *S. aureus* obtained by FISH analysis using magnetic particles.

FIG. 3 shows detection results of *S. aureus* obtained by FISH analysis using magnetic particles. A of FIG. 3 shows a photomicrograph confirming the results of FISH analysis using a common probe labeled with Cy3. B of FIG. 3 shows a photomicrograph confirming the results of FISH analysis using an *S. aureus* 16s rRNA-specific probe labeled with Cy5. C of FIG. 3 is a merge of images of A and B of FIG. 3.

As a result, it can be seen that, as shown in FIG. 3, by concentrating the microorganisms, various microorganisms present in the sample were detected without a process of purifying, culturing, or amplifying the nucleic acid, and from among the microorganisms, *S. aureus* could be specifically detected.

Example 3. Multiple FISH Analysis

By concentrating the microorganisms through Example 1, it was confirmed that the microorganisms could be effectively detected without purification, culturing, or amplification.

In order to concentrate the microorganisms in the sample and confirm that multiplex detection can be performed in the same sample, multiple FISH analysis was performed as follows.

For primary FISH analysis, immunostaining was performed using a Cy5-labeled *S. aureus* 16s rRNA-specific probe in a microfluidic channel concentrating microorganisms as in Example 1, and microorganisms were detected using a phase contrast microscope. For washing, a 40% formamide solution was flowed through the microfluidic channel to perform washing at 73° C. for 3 minutes. Microorganisms were detected under a fluorescence microscope to confirm that the washing was successful. For the secondary FISH analysis, after washing, immunostaining was performed using a Cy5-labeled *S. aureus* 16s rRNA-specific probe, and microorganisms were detected using a fluorescence microscope.

Figure 4:
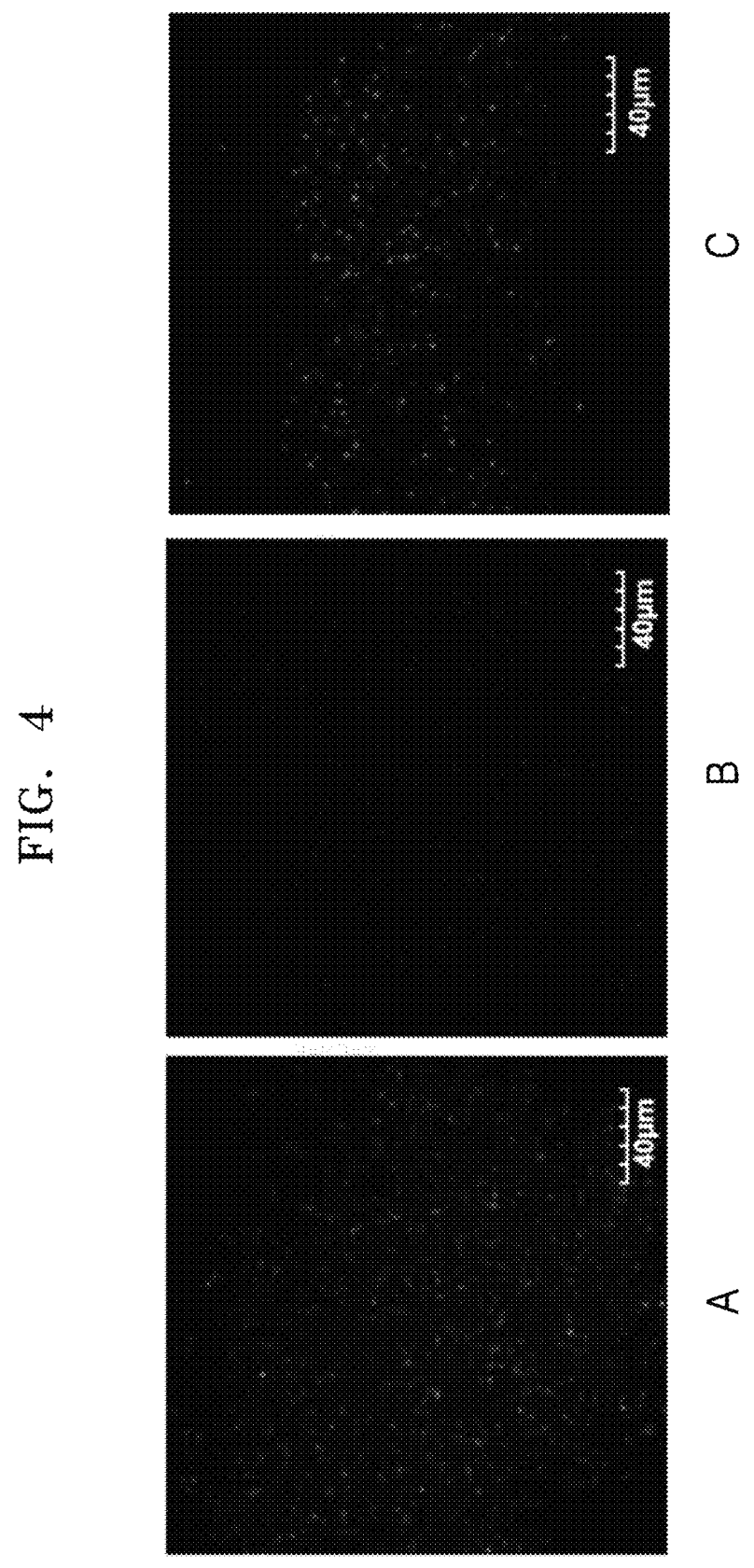

FIG. 4 shows fluorescence micrographs of primary FISH results for *S. aureus* (A), results of washing with formamide solution (B), and secondary FISH results for *S. aureus* (C).

As a result, as shown in A of FIG. 4, since the signal detected from the *S. aureus*-specific probe was confirmed, it was confirmed that *S. aureus* concentrated in the microfluidic channel could be effectively detected without a separate amplification process. In addition, as shown in B of FIG. 4, since almost no fluorescence signal was detected, it was confirmed that the washing efficiency obtained by the formamide treatment was excellent. In addition, as shown in C of FIG. 4, it was confirmed that the signal detected from the *S. aureus*-specific probe, which had disappeared by washing, was detected again.

As a result, it was confirmed that the signal by the fluorescent probe was reduced to a level similar to the noise level by washing with formamide. In addition, since microorganisms are fixed and concentrated by magnetic nanoparticles, it was confirmed that microorganisms may be repeatedly detected and identified in one sample using one or more types of fluorescent probes.

Example 4. Concentration and Detection of Microorganisms Using Centrifugation Samples treated as in Example 1.1 above were placed in EP tubes, concentrated using centrifugation, and subjected to multiplex FISH analysis.

In detail, for primary FISH analysis, immunostaining was performed using the Cy5-labeled *E. coli* 16s rRNA common probe (SEQ ID NO: 26: GGTGTGACGGGCGGTGTGTA-CAAG) in a tube in which microorganisms were concentrated, and microorganisms were detected under a phase contrast microscope.

Figure 5:
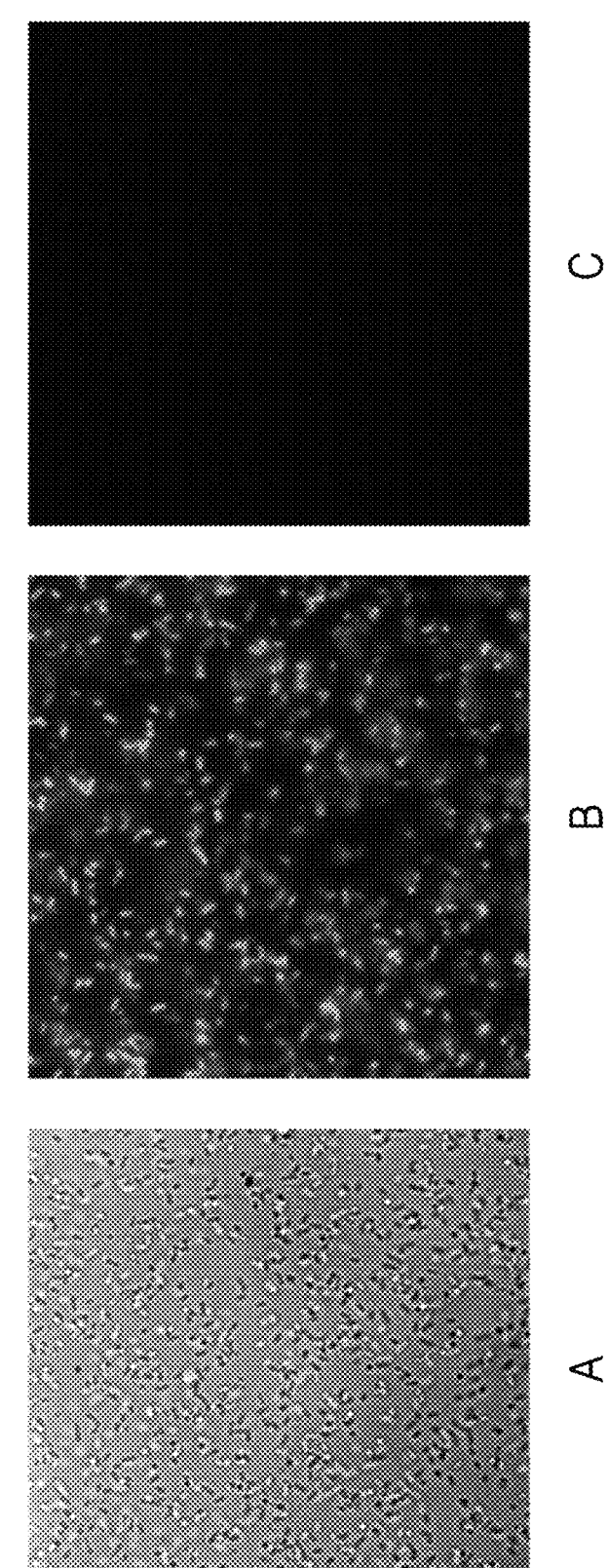
FIG. 5 shows a photograph of results of primary FISH analysis on *E. coli*: phase contrast microscopy (A), Cy5 fluorescence detection (B), and Cy3 fluorescence detection (C).

FIG. 5 shows a photograph of results of primary FISH analysis on *E. coli*: phase contrast microscopy (A), Cy5 fluorescence detection (B), and Cy3 fluorescence detection (C).

For the secondary FISH analysis, the tubes were washed by flushing with a 40% formamide solution. After washing, immunostaining was performed using a Cy3-labeled *E. coli* 16s rRNA common probe (SEQ ID NO: 26: GGTGTGACGGGCGGTGTGTACAAG), and microorganisms were detected using a phase contrast microscope.

Figure 6:
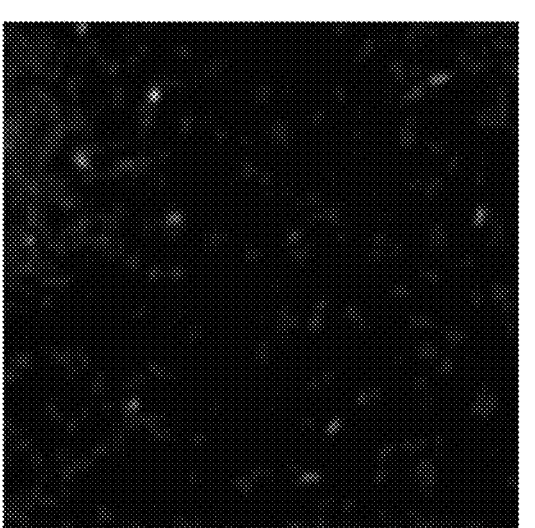
FIG. 6 shows a photograph of results of secondary FISH analysis on *E. coli*: phase contrast microscopy (A), Cy3 fluorescence detection (B), and Cy5 fluorescence detection (C).
Figure 6:
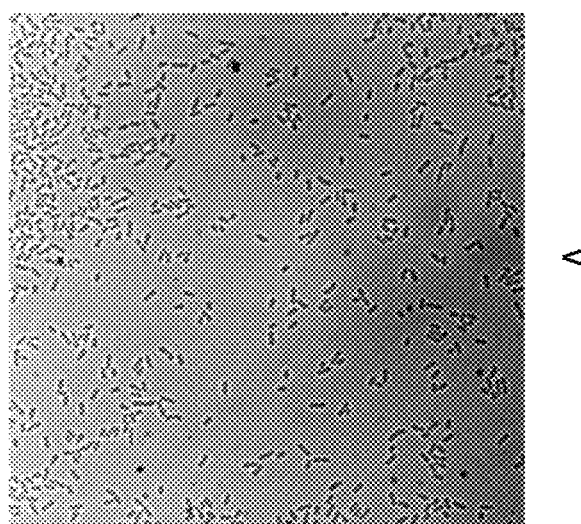

FIG. 6 shows a photograph of results of secondary FISH analysis on *E. coli*: phase contrast microscopy (A), Cy3 fluorescence detection (B), and Cy5 fluorescence detection (C).

For the tertiary FISH analysis, the tube was washed by flushing with a 40% formamide solution. After washing, immunostaining was performed using a Cy5-labeled *E. coli* 16s rRNA common probe (SEQ ID NO: 26: GGTGTGACGGGCGGTGTGTACAAG), and microorganisms were detected using a phase contrast microscope.

Figure 7:
FIG. 7 shows a photograph of results of tertiary FISH analysis on *E. coli*: phase contrast microscopy (A), Cy5 fluorescence detection (B), and Cy3 fluorescence detection (C).
Figure 7:
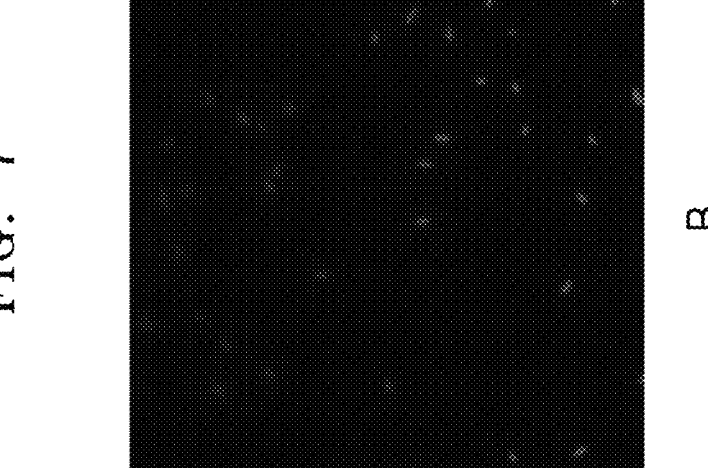
Figure 7:
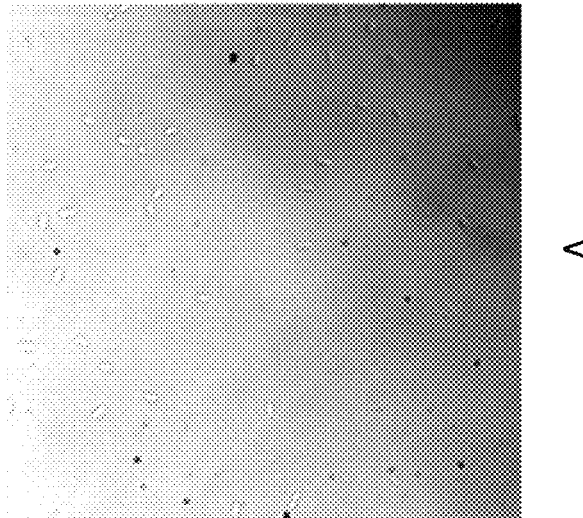

FIG. 7 shows a photograph of results of tertiary FISH analysis on *E. coli*: phase contrast microscopy (A), Cy5 fluorescence detection (B), and Cy3 fluorescence detection (C).

For the tertiary FISH analysis, the tube was washed by flushing with a 40% formamide solution. After washing, immunostaining was performed using a Cy3-labeled *E. coli* 16s rRNA common probe (SEQ ID NO: 26: GGTGTGACGGGCGGTGTGTACAAG), and microorganisms were detected using a phase contrast microscope.

Figure 8:
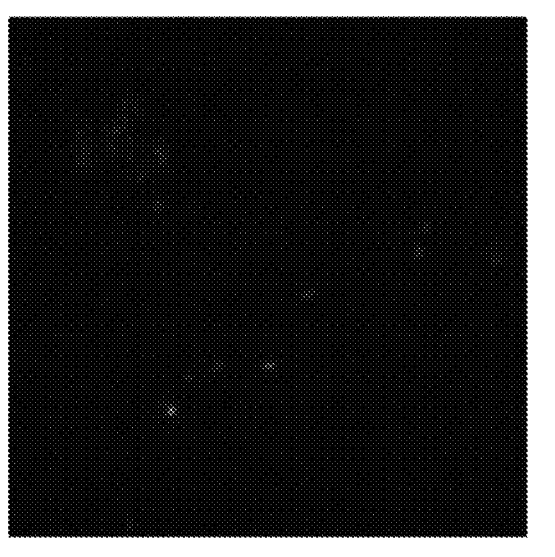
FIG. 8 shows a photograph of results of quaternary FISH analysis on *E. coli*: phase contrast microscopy (A), Cy3 fluorescence detection (B), and Cy5 fluorescence detection (C).
Figure 8:
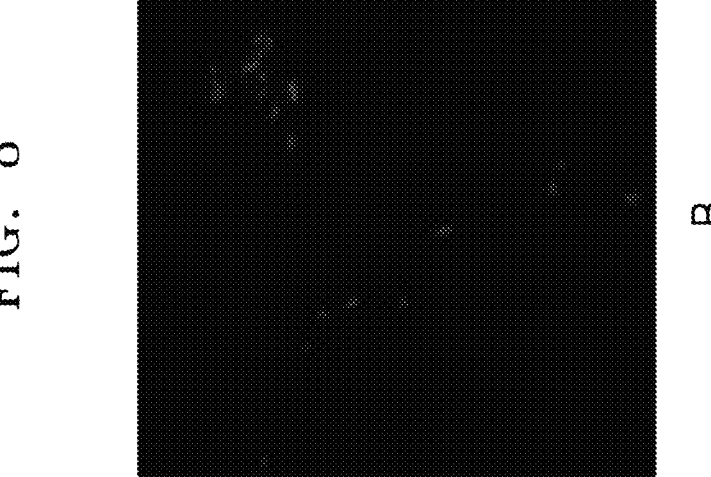
Figure 8:
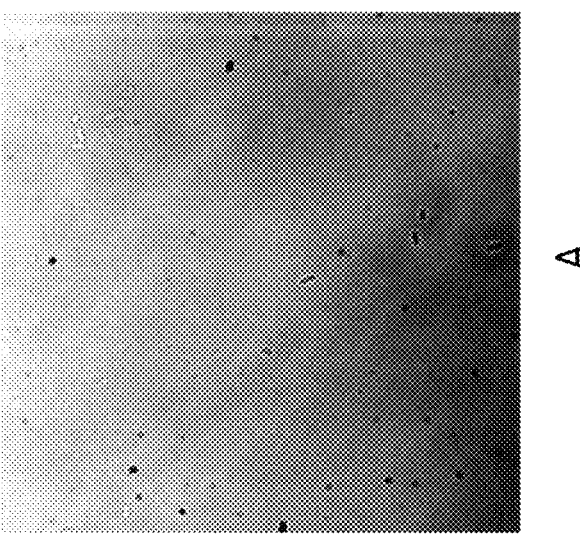

FIG. 8 shows a photograph of results of quaternary FISH analysis on *E. coli*: phase contrast microscopy (A), Cy3 fluorescence detection (B), and Cy5 fluorescence detection (C).

For the results, the results of performing multiple FISH analyzes were analyzed with Image J.

Figure 9:
FIG. 9 shows a graph of the results of multiple FISH analysis for *E. coli* obtained by Image J (n=10).

FIG. 9 shows a graph of the results of multiple FISH analysis for *E. coli* obtained by Image J (n=10).

As a result, as shown in FIG. 9, it was confirmed that the signal by the fluorescent probe was reduced to a level similar to the noise level by washing with formamide. In addition, since microorganisms are fixed and concentrated by centrifugation, it was confirmed that microorganisms may be repeatedly detected and identified in one sample using one or more types of fluorescent probes.

II. Optimization of the FISH Analysis

Comparative Example 1. Detection of *S. aureus* Through FISH Analysis

In order to evaluate the efficiency of detecting *S. aureus* through the conventional FISH analysis method, microorganism samples were analyzed as *S. aureus*.

1.1. Washing the Detection Device

A microfluidic channel, a 20×40×0.2 mm rectangular polydimethylsiloxane (PDMS) channel, was used as a microorganism detection device. To wash the microfluidic channel, 99.9% (v/v) ethanol at a rate of 10 µl/min for 10 minutes, distilled water at a rate of 10 µl/min for 10 minutes, and 1× phosphate buffered saline (PBS) at a rate of 10 µl/min for 10 minutes were sequentially flowed to the inlet of a microfluidic channel using a syringe pump or a pneumatic pump to wash the device.

1.2. Fixation and Permeabilization of Microorganisms

The body fluid containing *S. aureus* as a sample was flowed through the microfluidic channel washed as described above, and pathogenic microorganisms were captured.

For fixation and permeabilization of microorganisms in the captured sample, fixation of microorganisms was performed by treatment with 50% (v/v) cold ethanol at a rate of 10 µl/min for 10 minutes, 3.7% (v/v) formaldehyde at a rate of 10 µl/min for 4 minutes, and 1×PBS at a rate of 10 µl/min for 10 minutes, and permeabilization thereof was performed by treatment with 70% (v/v) ethanol at 10 µl/min for 4 min and at 1 µl/min for 60 minutes.

1.3. Probe Hybridization

In order to hybridize the probe to the microorganisms that have undergone fixation and permeabilization as described above, after flowing the Cy3- and Cy5-labeled probes for 10 minutes with 40% (v/v) formamide and 2×SSC at a rate of 10 µl/min, a hybridization solution was sequentially flowed for 2 hours at a rate of 5 µl/min to hybridize the probes to the microorganisms. Here, the hybridization solution contains 15% (v/v) ethylene carbonate, 20% (v/v) dextran sulfate, 600 mM NaCl, and 10 mM citrate, and has a pH of 6.2.

1.4. Staining and Imaging

When the probe was hybridized as described above, 2×SSC containing the fluorescent material DAPI, together with 40% (v/v) formamide, at 10 µl/min for 15 minutes, and 2×SSC at 10 µl/min for 10 minutes, were flowed sequentially. All procedures except for the treatment with hybridization solution were performed at room temperature. Treatment of the hybridization solution was performed at 45° C. The microorganisms treated as described above were imaged with a fluorescence microscope to detect microorganisms. DAPI is a fluorescent material located between the double-stranded DNA of all bacteria to stain unspecific DNA, Cy3 is a fluorescent material to stain a probe specific to a sequence common to bacteria, and Cy5 is a fluorescent material for staining the probe that binds to a sequence specifically present in *S. aureus*. Microbial detection results are shown in FIG. 10.

FISH efficiency for *S. aureus* was evaluated by measuring the number of merged fluorescent signals from Cy5 staining for *S. aureus* relative to the number of fluorescent signals from DAPI that stains all bacteria in the sample.

Figure 10:
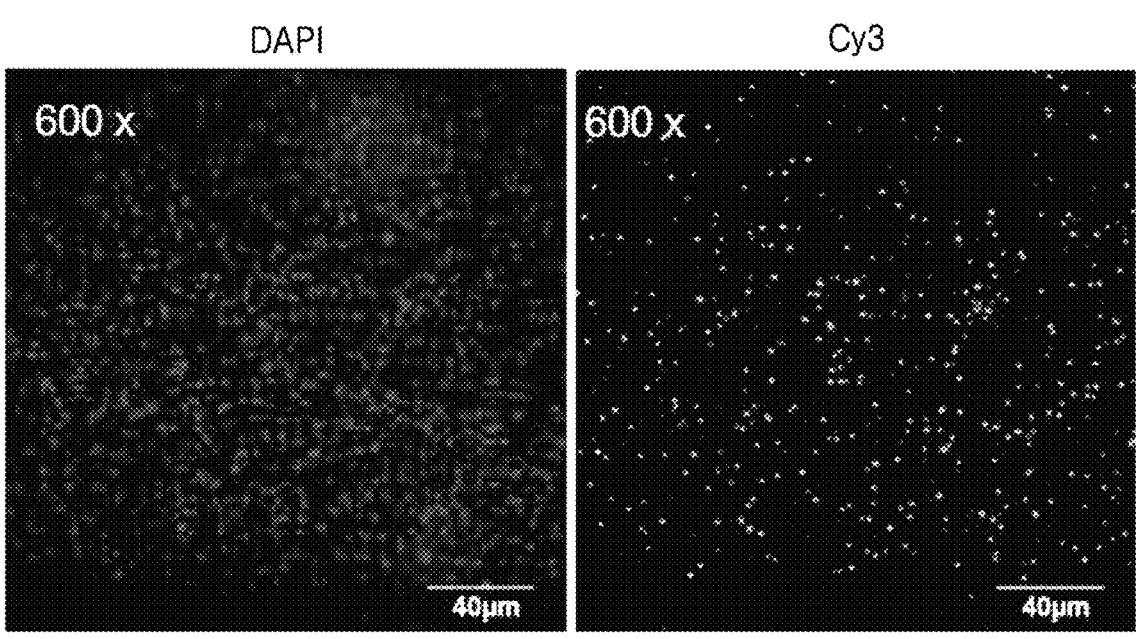
FIG. 10 shows FISH analysis images of *S. aureus* obtained by a conventional method.
Figure 10:
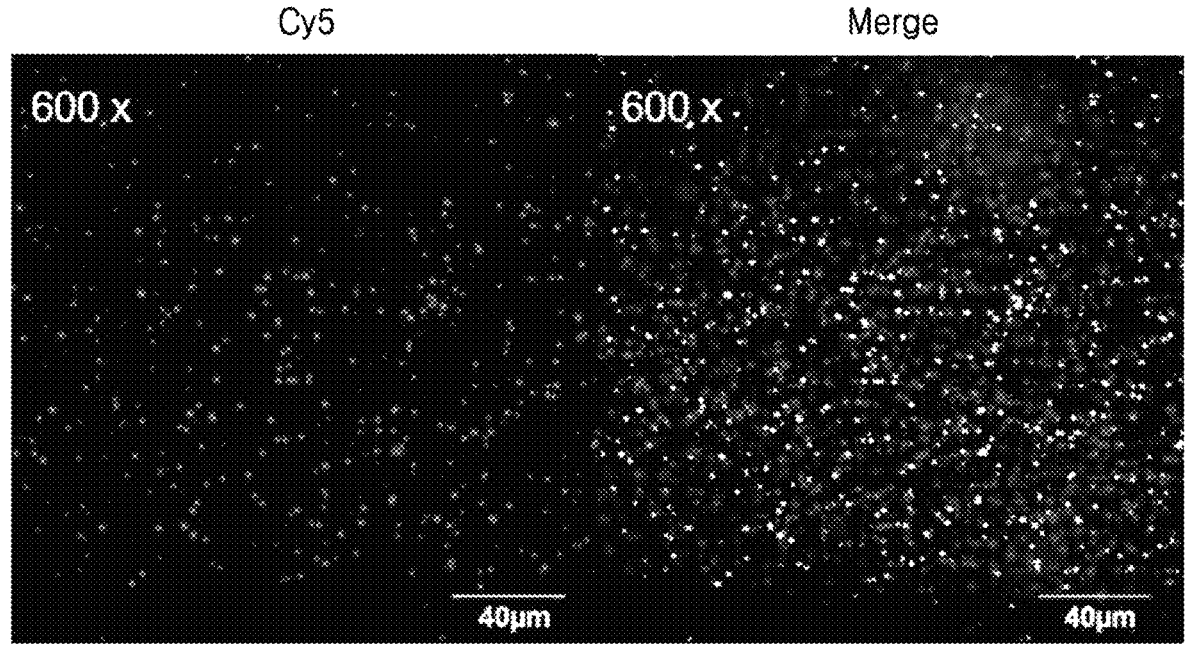

FIG. 10 shows FISH analysis images of *S. aureus* obtained by a conventional method.

As a result, as shown in FIG. 10, the FISH efficiency for *S. aureus* was confirmed to be 36%.

Comparative Example 2. Detection of *E. coli* by FISH Analysis

In order to evaluate the efficiency of detecting *E. coli* through the conventional FISH analysis method, FISH analysis was performed in the same manner as in Comparative Example 1 using *E. coli* as a microbial sample. Cy5 is a fluorescent material for staining a probe that binds to a sequence specifically present in *E. coli*. Microbial detection results are shown in FIG. 11.

FISH efficiency for *E. coli* was evaluated by measuring the number of merged fluorescent signals from Cy5 staining for *E. coli* relative to the number of fluorescent signals from DAPI that stains all bacteria in the sample.

Figure 11:
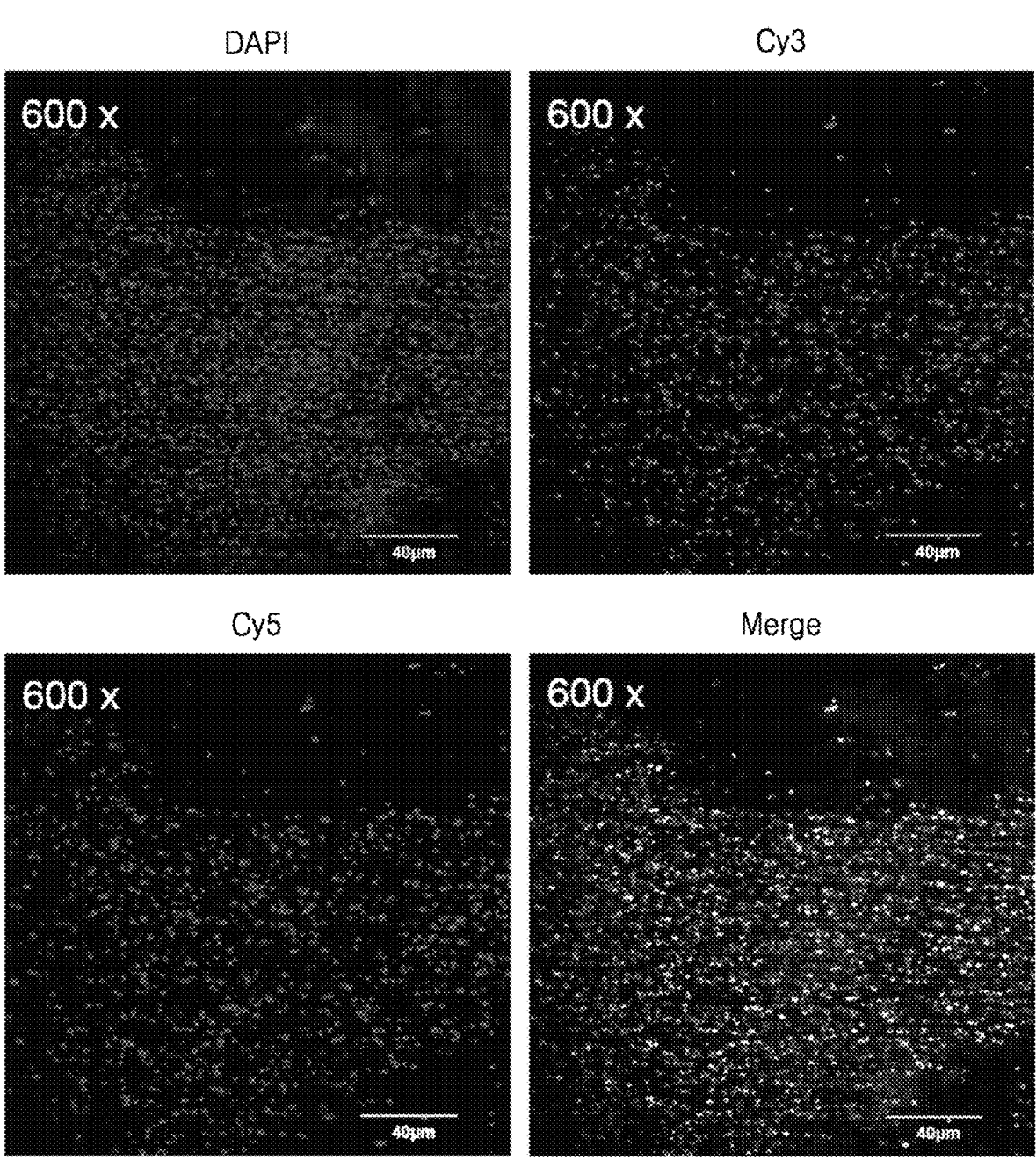
FIG. 11 shows FISH analysis images of *E. coli* obtained by a conventional method.

FIG. 11 shows FISH analysis images of *E. coli* obtained by a conventional method.

As a result, as shown in FIG. 11, it was confirmed that the FISH efficiency for *E. coli* was 95% or more.

Through Comparative Examples 1 and 2, it can be seen that the efficiency of detecting gram-negative bacteria was excellent in the case of the conventional FISH analysis method, but the efficiency of detecting gram-positive bacteria was very poor.

Example 5. Evaluation of Detection Efficiency of *S. aureus* Through FISH Analysis of Present Disclosure From the results of Comparative Examples 1 and 2, it was confirmed that the efficiency of detecting *S. aureus*, a gram-positive bacteria, by the FISH analysis of the related art was not good, so the microorganisms fixation and permeabilization methods were optimized to increase the detection efficiency of *S. aureus*.

5.1. Washing the Detection Device

This experiment was performed in the same manner as in Comparative Example 1.

5.2. Fixation and Permeabilization of Microorganisms

For fixation and permeabilization of microorganisms in the captured sample, microorganisms were treated by flowing 1×PBS at a rate of 10 μl/min for 10 minutes, 24% (v/v) ethanol at a rate of 10 μl/min for 10 minutes, 1×PBS at a rate of 10 μl/min for 10 minutes, 99.9% (v/v) methanol at a rate of 10 μl/min for 10 minutes, and 1×PBS at a rate of 10 μl/min for 10 minutes in this order.

5.3. Probe Hybridization

This experiment was performed in the same manner as in Comparative Example 1.

5.4. Staining and Imaging

When the probe was hybridized as described above, 2×SSC containing the fluorescent material DAPI, together with, 40% (v/v) formamide, at 10 μl/min for 15 minutes, and 2×SSC at 10 μl/min for 10 minutes, were sequentially flowed. All procedures except for the treatment with hybridization solution were performed at room temperature. Treatment of the hybridization solution was performed at 45° C. Microorganisms treated as described above were imaged with a fluorescence microscope to detect microorganisms. DAPI is a fluorescent material located between the double-stranded DNA of all bacteria to stain unspecific DNA, and Cy5 is a fluorescent material for staining the probe that binds specifically to S. aureus. Microbial detection results are shown in FIG. 12.

FISH efficiency for S. aureus was evaluated by measuring the number of overlapping fluorescent signals from DAPI, which stained all bacteria contained in the sample, versus the number of overlapping fluorescent signals from Cy5, which stained S. aureus.

Figure 12:
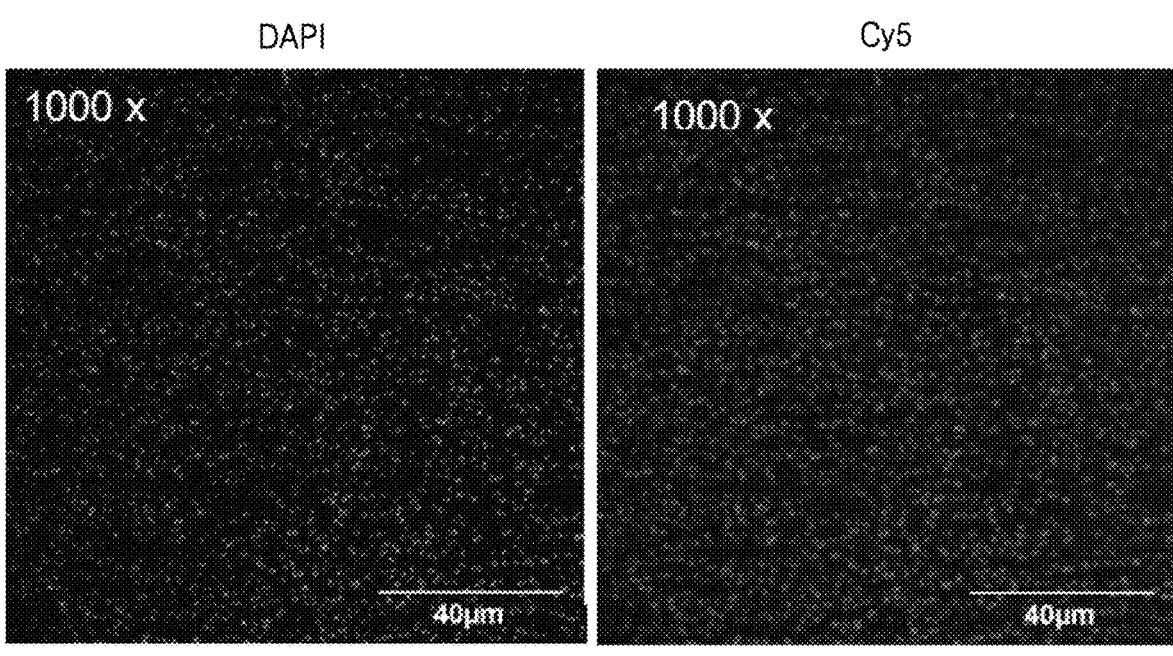
FIG. 12 shows FISH analysis images of *S. aureus* obtained by a method of the present disclosure.
Figure 12:
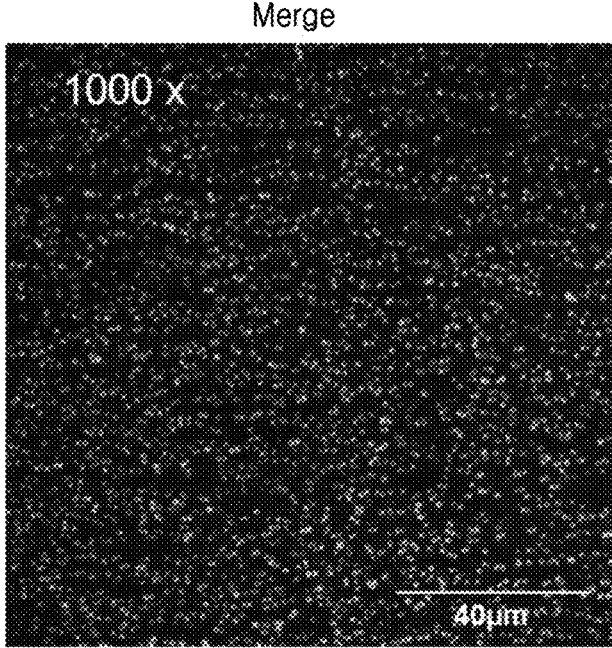

FIG. 12 shows FISH analysis images of S. aureus obtained by a method of the present disclosure.

As a result, as shown in FIG. 12, the FISH efficiency for S. aureus was confirmed to be 96% or more.

Therefore, it was confirmed that when FISH analysis was performed according to an embodiment method, S. aureus, which had poor detection efficiency by the conventional FISH method, could be detected with high efficiency.

III. Evaluation of Antibiotic Susceptibility of Microorganisms Using FISH Analysis Example 6. Classification and Preparation of Test Microorganisms In this example, a total of two experiments were conducted on each of E. coli K-12 bacteria as test microorganisms having antibiotic susceptibility, and E. coli ER7 bacteria as test microorganisms having antibiotic resistance, and each group was set to include E. faecalis bacteria having resistance to Cefotaxime.

6.1. Classification of Microbial Groups

In this example, in order to evaluate the test antibiotic susceptibility of microorganisms, microbial groups including test microorganisms were classified into three groups.

Figure 13:
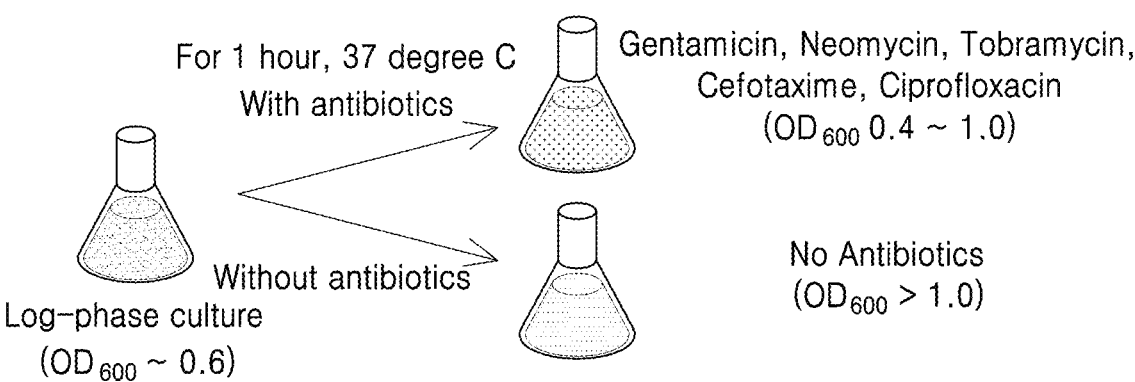
FIG. 13 shows a schematic diagram illustrating a process of obtaining a first microbial group and a second microbial group, each including test microorganisms, in an antibiotic susceptibility evaluation method according to an embodiment.

FIG. 13 shows a schematic diagram illustrating a process of obtaining a first microbial group and a second microbial group, each including test microorganisms, in an antibiotic susceptibility evaluation method according to an embodiment.

In an embodiment, as shown in FIG. 13, microbial groups were classified as follows: a first microbial group was obtained by culturing for about 1 hour by adding the antibiotic cefotaxime to a medium containing test microorganisms; a second microbial group was obtained by culturing for about 1 hour by adding saline to a medium containing test microorganisms; and a third microbial group was obtained without culturing of a medium including test microorganisms. The number or ratio of initial microorganisms in the first microbial group, the second microbial group, and the third microbial group was set identically.

6.2. Preparation of Samples Containing Test Microorganisms

In this example, a sample containing test microorganisms was prepared to enable evaluation of antibiotic susceptibility of test microorganisms.

In an embodiment, E. coli K-12 bacteria, antibiotic-resistant E. coli ER7 bacteria, and E. faecalis resistant to cefotaxime were used, and each strain was cultured up to OD 600=0.5 to obtain a sample containing the test microorganisms. On the other hand, after treating the sample with antibiotics, the amount of the test microorganisms was quantified by imaging at OD 600. In this case, the imaging process was performed by centrifugation at 3,000 g for 3 min, concentrating the sample 10-fold and fixing the same on a glass substrate coated with Vectabond.

Example 7. Antibiotic Susceptibility Evaluation Through FISH Analysis

In this example, the ratio of the test microorganisms in the classified and obtained microbial groups was quantified, and based thereon, the antibiotic susceptibility of test microorganisms was evaluated.

To fix bacterial samples, a 50:1 solution of acetone and Vectabond was dropped onto a sample dish. Next, the sample dish was incubated at room temperature for 5 minutes, and washed 2 to 3 times with tertiary water, and then the water was completely removed therefrom. Thereafter, the test microorganisms samples of Example 6 were dropped on the coated sample dish, and incubated at room temperature for 30 minutes, and the remaining sample was washed three times. Next, a 3.7% formaldehyde solution was dropped on the sample dish on which the sample was fixed, and then the fixation was performed for 30 minutes at room temperature. Afterwards, it was washed 2 to 3 times with nuclease-free tertiary water. Next, in order to increase the bacterial permeability of the PNA probe, the resultant sample was treated with 5 mg/ml of nuclease-free tertiary lysozyme and incubated at 37° C. for 30 minutes. Next, the bacterial sample fixed on the bottom of the sample dish was treated, at 55° C. for 30 minutes, with 100 μL of a mixed solution including 10% (wt/vol) dextran sulfate, 10 mM NaCl, 30% (vol/vol) formamide, 0.1% (vol/vol) triton X-100, 50 mM tris-HCl (pH 7.5), 0.2% (wt/vol) polyvinylpyrrolidone, 0.2% (wt/vol) Ficoll, 0.1% (wt/vol) sodium pyrophosphate, 5 mM disodium EDTA, 100 nM E. coli PNA probe, and 100 nM E. faecalis PNA probe. Thereafter, 200 μL of washing solution containing 15% (vol/vol) formamide, 5 mM tris base, 15 mM NaCl, and 0.1% Hoechst 33342 was applied twice at 55° C. for 15 minutes to wash away residual PNA probes, and washed using 1×PBS solution diluted with nuclease-free tertiary lysozyme. Finally, after immersing the sample in a 2×SSC solution diluted with nuclease-free tertiary lysozyme, a fluorescence image of the sample was acquired using a confocal fluorescence microscope.

Figure 14:
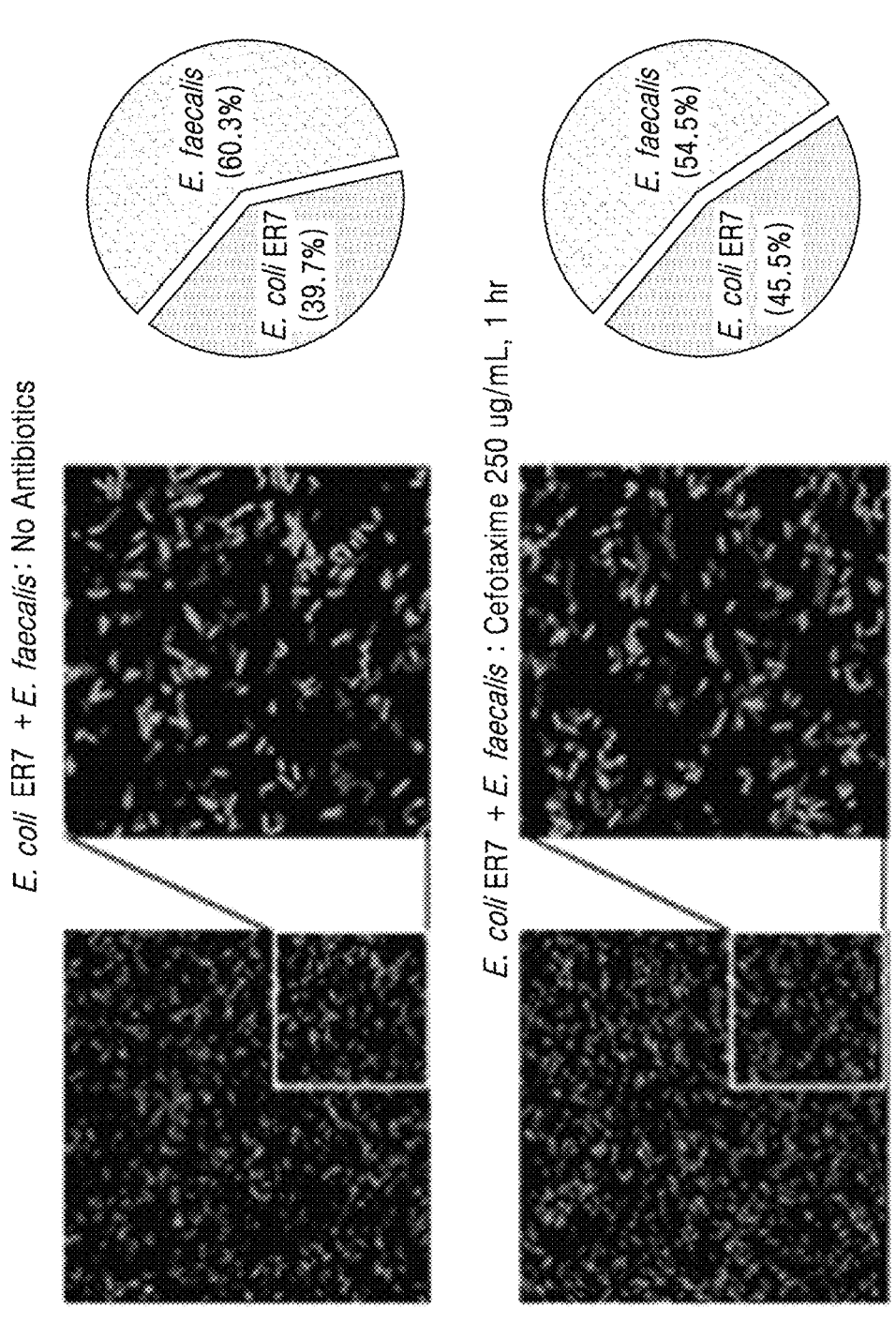
FIG. 14 shows a diagram showing evaluation results for a sample including test microorganisms that do not have antibiotic susceptibility, obtained by an antibiotic susceptibility evaluation method according to an embodiment.

FIG. 14 shows a diagram showing evaluation results for a sample including test microorganisms that do not have antibiotic susceptibility, obtained by an antibiotic susceptibility evaluation method according to an embodiment.

Figure 15:
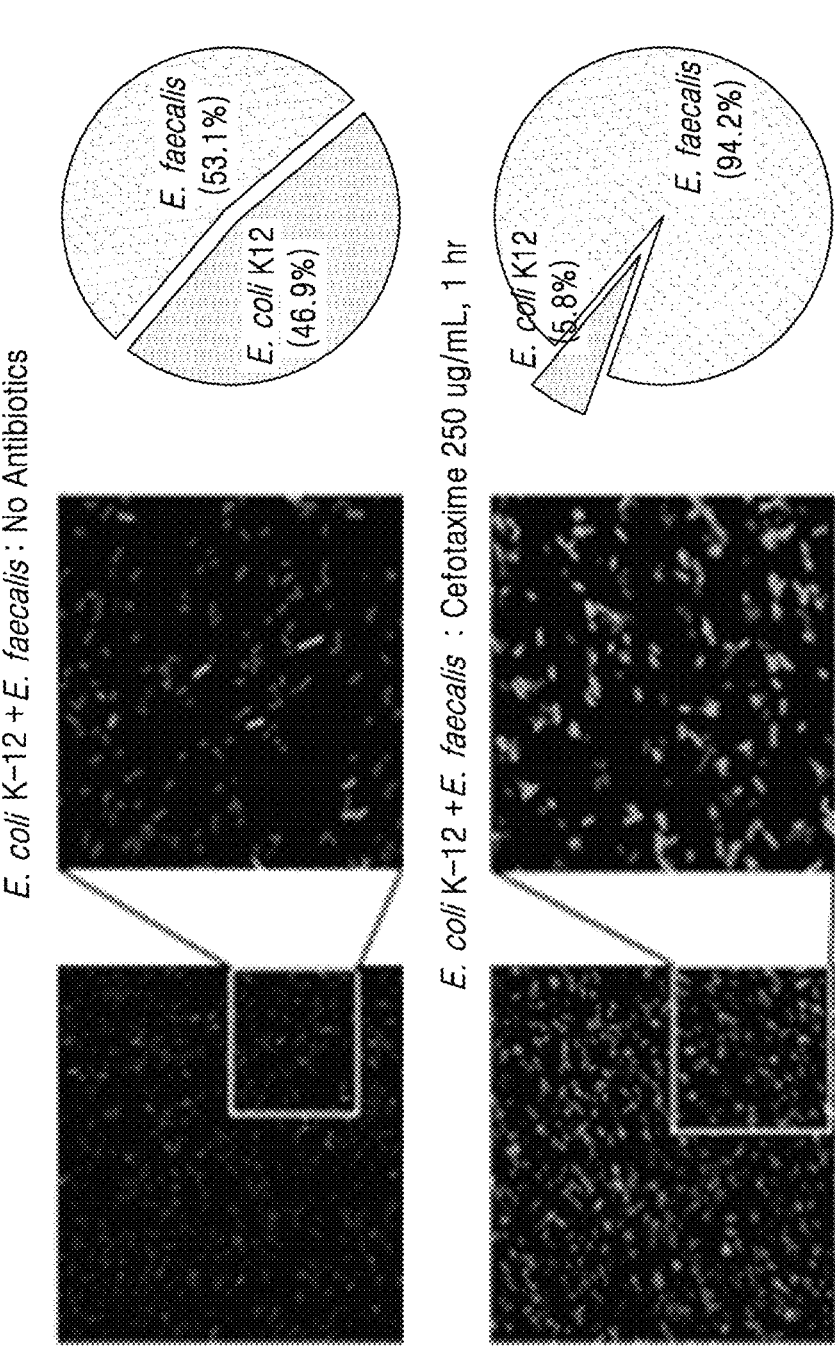
FIG. 15 shows a diagram showing evaluation results for a sample including test microorganisms that have antibiotic susceptibility, obtained by an antibiotic susceptibility evaluation method according to an embodiment.

FIG. 15 shows a diagram showing evaluation results for a sample including test microorganisms that have antibiotic susceptibility, obtained by an antibiotic susceptibility evaluation method according to an embodiment.

As shown in FIG. 14, in the case of test microorganisms without antibiotic susceptibility, the ratio of test microorganisms in the first microbial group was maintained, whereas as shown in FIG. 15, in the case of test microorganisms with antibiotic susceptibility, the ratio of the test microorganisms in the first microbial group was decreased. These results indicate that the sensitivity of the test microorganisms can be confirmed in a short time by measuring the ratio of the test microorganisms to the total bacteria.

Figure 16:
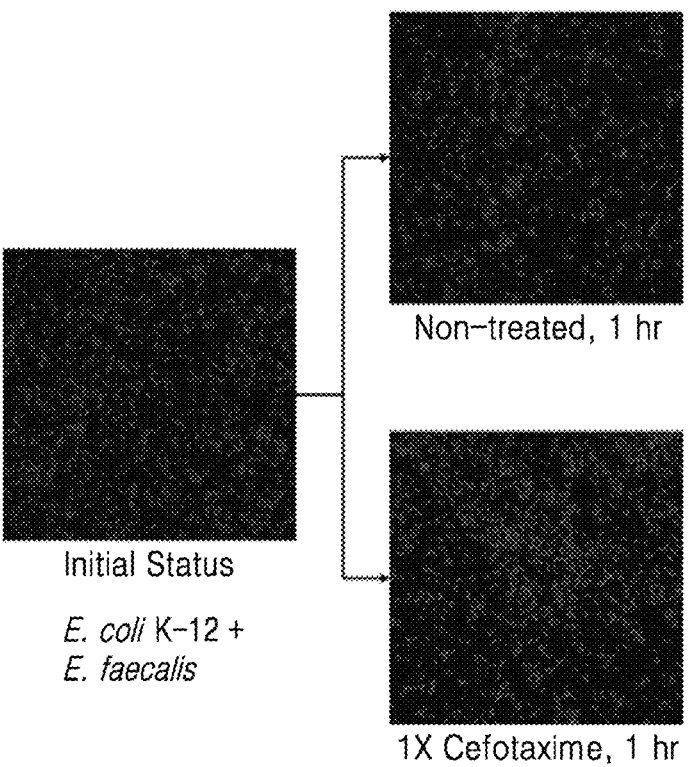
FIG. 16 shows antibiotic susceptibility evaluation results obtained by using a first microbial group, a second microbial group, and a third microbial group through an antibiotic susceptibility evaluation method.

FIG. 16 shows antibiotic susceptibility evaluation results obtained by using a first microbial group, a second microbial group, and a third microbial group through an antibiotic susceptibility evaluation method.

Figure 17:
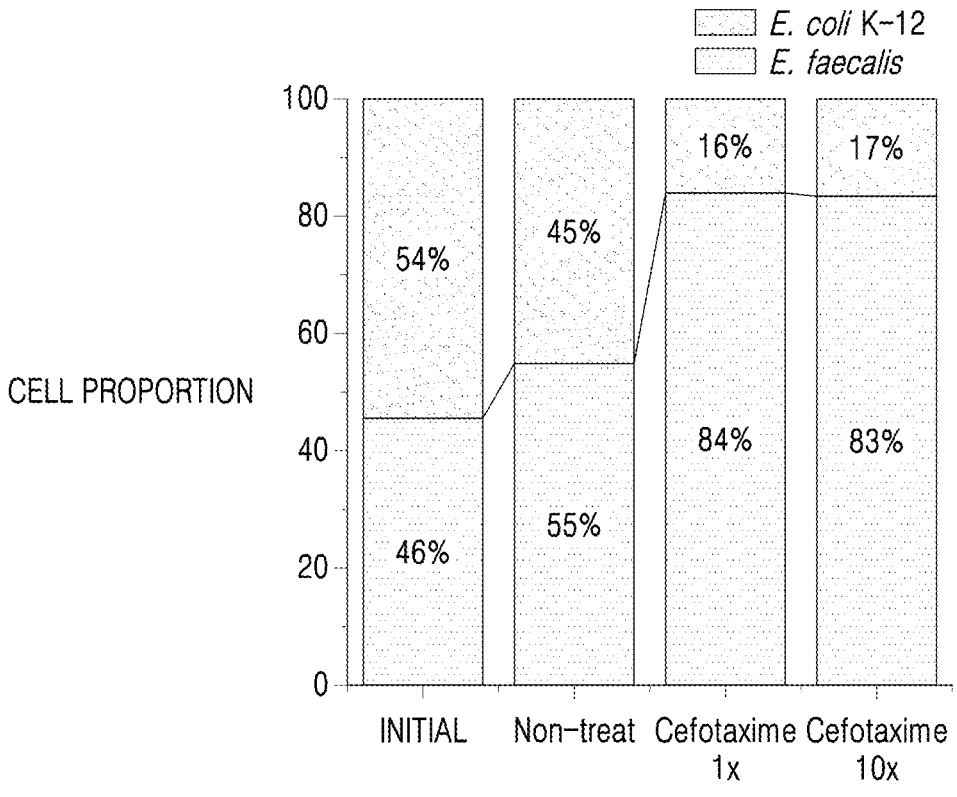
FIG. 17 shows antibiotic susceptibility quantitative evaluation results obtained by using a first microbial group, a second microbial group, and a third microbial group through an antibiotic susceptibility evaluation method.

FIG. 17 shows antibiotic susceptibility quantitative evaluation results obtained by using a first microbial group, a second microbial group, and a third microbial group through an antibiotic susceptibility evaluation method.

In an embodiment, as shown in FIGS. 16 and 17, the sample in which the two microorganisms (*E. coli* and *E. faecalis*) groups are mixed, was classified into first, second, and third microbial groups, and the first microbial group was treated with antibiotic (cefotaxime) and cultured for 1 hour. As a result, it was confirmed that the ratio of *E. coli* and *E. faecalis* changed.

In general, the growth rate may vary depending on the growth rate and physiological state of each microorganism, but it is expected that the individual differences in the groups will not be large after 1 hour of culturing. However, when various species of microorganisms are mixed, there is a probability that the entire group will not grow uniformly under those conditions. In one aspect of the antibiotic susceptibility evaluation method, the comparing the ratio of test microorganisms in the second microbial group and the third microbial group, performed for additional verification of microorganisms showing changes in the first microbial group treated with antibiotics, may serve to evaluating the difference among microorganisms that may occur during culturing of microbial groups.

In this example, it was confirmed that there was no significant difference in the amount or ratio of microorganisms between the third microbial group, which is an initial microbial group, and the second microbial group cultured without antibiotics. Therefore, while assuming that resistant bacteria and susceptible bacteria included in each microbial group were cultured without significant differences under the given culture conditions, antibiotic susceptibility was evaluated. However, even when evaluating a microbial group containing two or more species of microorganisms showing a difference in growth under the corresponding culture conditions, the difference can be corrected through such comparison.

As a result, as shown in FIGS. 16 and 17, in the case of the first microbial group treated and cultured with antibiotics, the number of population of *E. coli* K-12 exhibiting antibiotic susceptibility was rapidly reduced, whereas *E. faecalis* showing resistance continued to grow, confirming that the ratio changed significantly.

These results indicate that when the ratio of test microorganisms in the first microbial group is lower than that in the second microbial group, the test microorganisms have antibiotic susceptibility, and the ratio of test microorganisms in the first microbial group is equal to or higher than that of the second microbial group, the test have antibiotic resistance. Additionally, a significant difference in the ratio of microorganisms when comparing the second microbial group and the third microbial group, may indicate that there is a problem in the culture.

Therefore, according to the evaluation method of the present disclosure, antibiotic susceptibility of test microorganisms can be rapidly and accurately determined with only about 1 hour of culturing even in a sample containing one or more types of microorganisms, without lowering the accuracy of the antibiotic susceptibility test due to problems in culture.

IV. Detection of Microorganisms Through Multiple FISH Analysis Using Degradable PNA Probe

Example 8. FISH Analysis Based on Peptide Nucleic Acid (PNA) Probes

To detect or identify *S. aureus* species with low probe permeability, FISH analysis was performed using a PNA probe and an existing DNA probe, and the detection efficiencies of both were compared.

First, in order to detect or identify *S. aureus* species in the sample, the microorganisms of the sample were subjected to concentration, fixation, and permeabilization. In detail, the sample was centrifuged to concentrate microorganisms in the sample. In addition, the surface of the slide was coated with poly-l-lysine, the concentrated microorganisms were fixed on the surface of the slide, and then the fixation of the microorganisms was performed on the slide surface by treating the microorganisms with about 3.7% formaldehyde solution for about 30 minutes. Thereafter, permeabilization was performed on the microorganisms for about 30 minutes using a solution of about 5 mg/mL lysozyme as a cell permeability reagent.

Thereafter, the permeabilized microorganisms were hybridized with a PNA probe or a DNA probe. In an embodiment, a fluorescent material-labeled PNA probe or DNA probe was mixed with 10% (wt/vol) dextran sulfate, 10 mM NaCl, 30% (vol/vol) formamide, 0.1% (vol/vol) Triton X-100, 50 mM Tris-HCl (pH 7.5), 0.2% (wt/vol) polyvinylpyrrolidone, 0.2% (wt/vol) Ficoll, 0.1% (wt/vol) sodium pyrophosphate, and 5 mM disodium EDTA, and the permeabilized microorganisms were treated with 100 μL of the mixed solution at about 55° C. for about 30 minutes. Thereafter, the microorganisms were washed to remove probes that did not hybridize with the target, and the designated areas were imaged with a confocal microscope.

Figure 18:
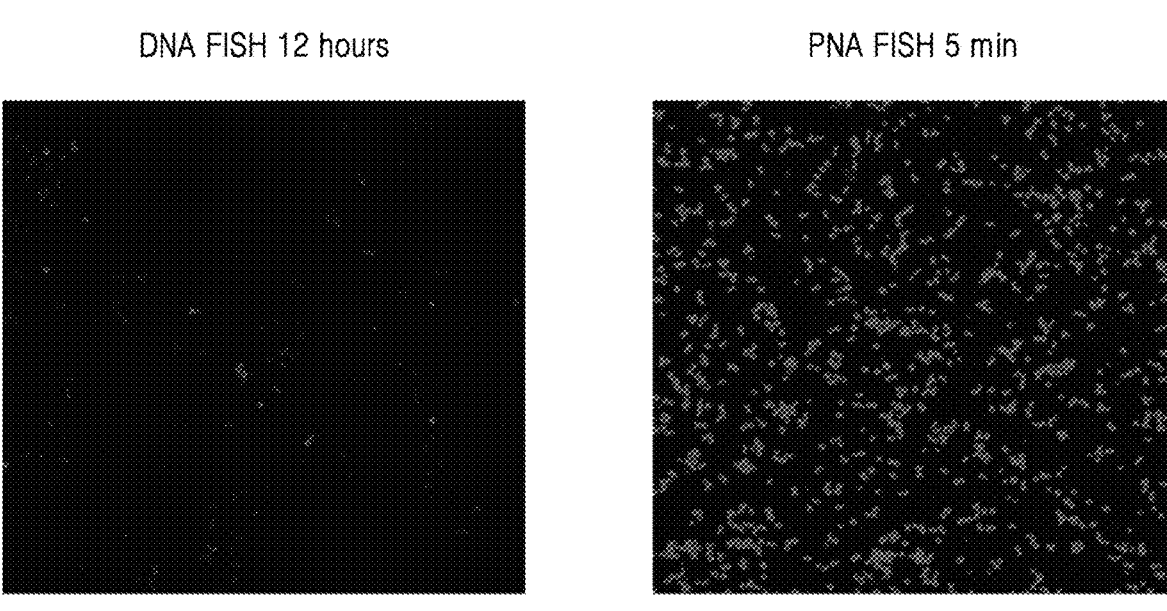
FIG. 18 is a diagram showing FISH analysis results obtained using a PNA probe or DNA probe on *S. aureus*.

FIG. 18 is a diagram showing FISH analysis results obtained using a PNA probe or DNA probe on *S. aureus*.

Figure 19:
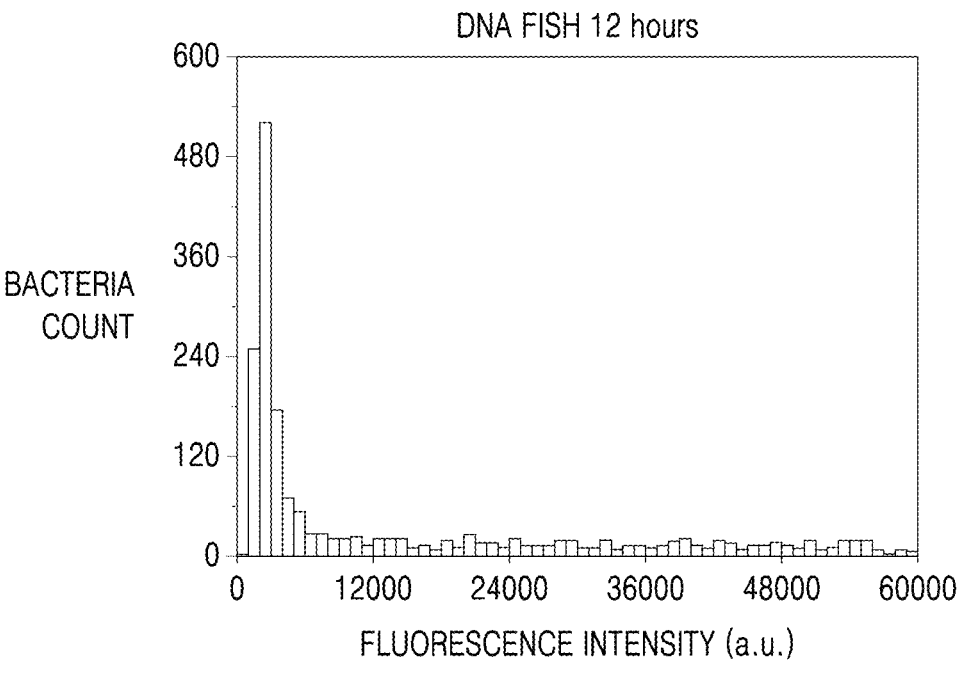
FIG. 19 is a graph showing the quantitative analysis results of the results of FIG. 18.
Figure 19:
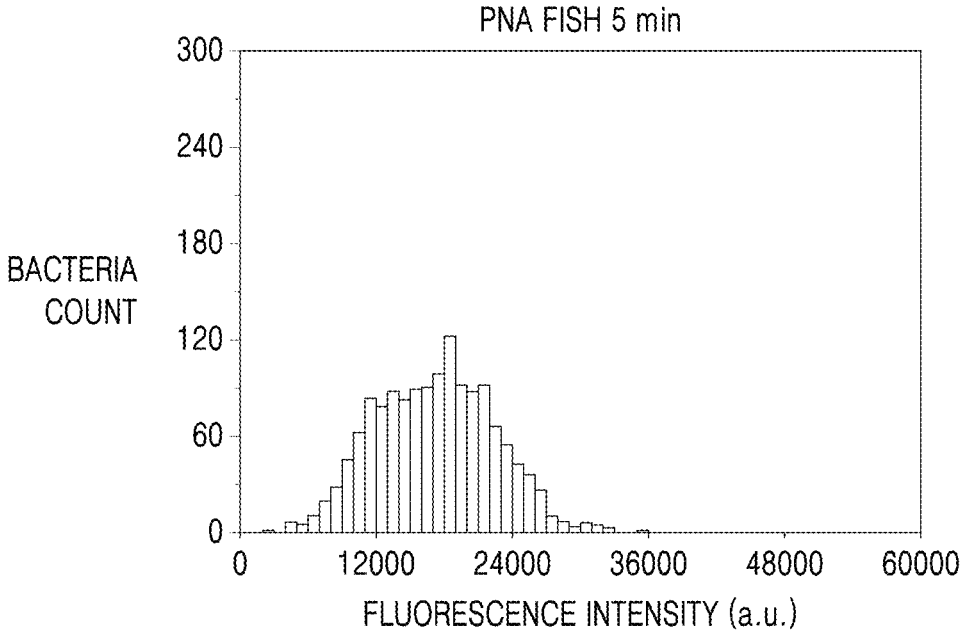

FIG. 19 is a graph showing the quantitative analysis results of the results of FIG. 18.

As a result, as shown in FIGS. 18 and 19, when the conventional DNA probe was used, detection efficiency was low even after hybridization for about 12 hours, whereas when the PNA probe was used, significantly increased detection efficiency was obtained after hybridization for only about 5 minutes.

Through this example, it was confirmed that the PNA probe-based FISH analysis method can significantly reduce the time required to detect or identify specific microorganism species compared to the conventional DNA probe-based FISH analysis method. This indicates that PNA probes exhibit better species specificity compared to traditional DNA probes. In addition, compared to conventional DNA probes, PNA probes penetrate into microorganisms more quickly and recognize ribosomal RNA sequences, which means that the time required to identify the species can be significantly reduced.

Example 9. Preparation of Biodegradable PNA
Probes

In order to increase the efficiency of the FISH analysis, a degradable PNA probe was prepared by labeling a fluorescent material on a PNA probe showing significantly better detection efficiency than conventional DNA probes. 5

First, a plurality of PNA probes capable of specifically detecting various microorganism species were prepared, and are shown in Table 1.

TABLE 1

| PNA Probe | Nucleotide sequence (5' → 3') | Target strain |
|---|---|---|
| 1 | AGGAAGGGAGTAAAG (SEQ ID NO: 1) | *Escherichia coli, Escherichia dysenteriae, Escherichia flexneri, or Escherichia marmotae* |
| 2 | GCGGTAGCACAGAGA (SEQ ID NO: 2) | *Klebsiella pneumoniae, Klebsiella quasipneumoniae, Klebsiella variicola, Raoultella ornithinolytica, or Raoultella planticola* |
| 3 | AGCGGTAGCACAGAG (SEQ ID NO: 3) | *Klebsiella pneumoniae, Klebsiella quasipneumoniae, Klebsiella variicola, Raoultella ornithinolytica, or Raoultella planticola* |
| 4 | GAGCGGTAGCACAGA (SEQ ID NO: 4) | *Klebsiella pneumoniae, Klebsiella quasipneumoniae, Klebsiella variicola, Raoultella ornithinolytica, or Raoultella planticola* |
| 5 | ATGCCATCAGATGTG (SEQ ID NO: 5) | *Cronobacter sakazakii, Klebsiella aerogenes, Klebsiella pneumoniae, Klebsiella quasipneumoniae, Klebsiella variicola, Raoultella ornithinolytica, or Raoultella planticola* |
| 6 | CATGCCATCAGATGT (SEQ ID NO: 6) | *Cronobacter sakazakii, Klebsiella aerogenes, Klebsiella pneumoniae, Klebsiella quasipneumoniae, Klebsiella variicola, Raoultella ornithinolytica, or Raoultella planticola* |
| 7 | GGCCTCATGCCATCA (SEQ ID NO: 7) | *Cronobacter sakazakii, Edwardsiella piscicida, Klebsiella aerogenes, Klebsiella pneumoniae, Klebsiella quasipneumoniae, Klebsiella variicola, Raoultella ornithinolytica, or Raoultella planticola* |
| 8 | AACGGACGAGAAGCT (SEQ ID NO: 8) | *Staphylococcus argenteus or Staphylococcus aureus* |
| 9 | AAGTGAAAGACGGTC (SEQ ID NO: 9) | *Staphylococcus argenteus* |
| 10 | CCTGAGGGAGAAAGT (SEQ ID NO: 10) | *Pseudomonas aeruginosa* |
| 11 | CTACTGAGCTAGAGT (SEQ ID NO: 11) | *Pseudomonas aeruginosa* |
| 12 | AACGCTTCTTTCCTC (SEQ ID NO: 12) | *Enterococcus faecalis* |
| 13 | TCTTTCCTCCCGAGT (SEQ ID NO: 13) | *Enterococcus faecalis* |
| 14 | AGAAGAACAAGGACG (SEQ ID NO: 14) | *Enterococcus faecalis* |
| 15 | GCACTATCGGATGAA (SEQ ID NO: 15) | *Proteus mirabilis* |
| 16 | AAAAGGTGCACTTGC (SEQ ID NO: 16) | *Streptococcus pneumoniae* |
| 17 | CTTGCATCACTACCA (SEQ ID NO: 17) | *Streptococcus pneumoniae* |
| 18 | CCGCATGGTTTTGAT (SEQ ID NO: 18) | *Enterococcus faecium* |

TABLE 1-continued

| PNA Probe | Nucleotide sequence (5' → 3') | Target strain |
|---|---|---|
| 19 | ACCGCATAAGAGAGA (SEQ ID NO: 19) | *Streptococcus pyogenes* |
| 20 | CGCATAAGAGAGACT (SEQ ID NO: 20) | *Streptococcus pyogenes* |
| 21 | CCGCATAACAATGGA (SEQ ID NO: 21) | *Streptococcus thermophilus* |
| 22 | CGCATAACAATGGAT (SEQ ID NO: 22) | *Streptococcus thermophilus* |
| 23 | TGAAAGATGCAAGCG (SEQ ID NO: 23) | *Streptococcus mutans* |
| 24 | CAAGAACGTGTGTGA (SEQ ID NO: 24) | *Streptococcus mutans* |
| 25 | TGAGTCTTGTAGAGG (SEQ ID NO: 25) | *Salmonella enterica* |

Next, a degradable PNA probe was obtained by connecting the prepared PNA probe and the fluorescent material to each other using chemically easily separable degradable bonding method, that is, a disulfide bond.

When FISH analysis is performed using the degradable PNA probe, the fluorescence signal can be quickly removed without separating the PNA probe from the target RNA after hybridization. This significantly reduces the time of multiple FISH analysis performed in sequential repeats, which can significantly increase analysis efficiency. In this regard, it was described in more detail in Examples 10 and 11 below.

Example 10. FISH Analysis Based on Degradable PNA Probe

FISH analysis was performed using the degradable PNA probe.

In detail, in the same manner as in Example 8, the microorganisms of the sample were subjected to concentration, fixation, and permeabilization, followed by hybridization with an *E. coli* 16s rRNA-specific degradable PNA probe for about 5 minutes. Thereafter, the microorganisms were washed to remove probes that did not hybridize with the target species, and the designated area was imaged by confocal microscopy. Thereafter, the fluorescent material was separated from the probe hybridized with the target species by treatment with about 100 mM TCEP solution for about 1 minute, and the same area was imaged. As a result, it was found that the fluorescence signal disappeared.

Figure 20:
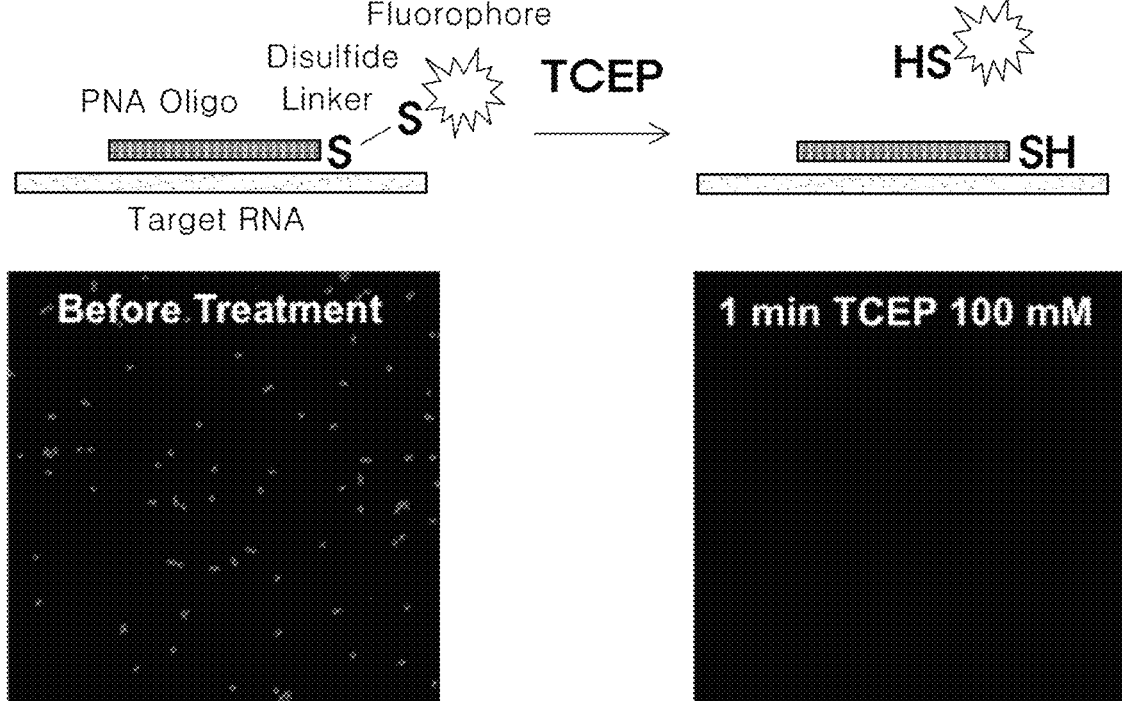
FIG. 20 is a diagram showing the results of a FISH analysis performed using a degradable PNA probe, in which a microorganism-specific fluorescence signal is detected and then, the fluorescence signal is removed.

FIG. 20 is a diagram showing the results of a FISH analysis performed using a degradable PNA probe, in which a microorganism-specific fluorescence signal is detected and then, the fluorescence signal is removed.

Figure 21:
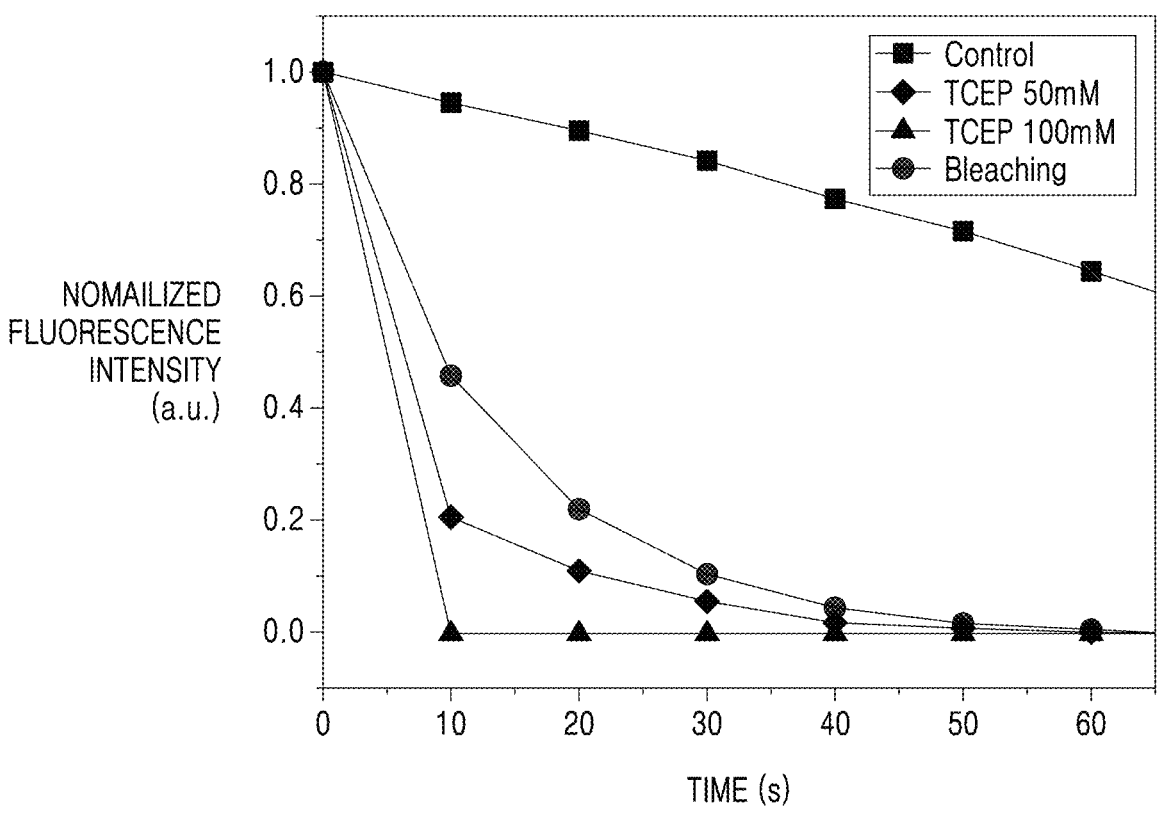
FIG. 21 is a diagram showing analysis results for the time required to remove the fluorescence signal based on the results of FIG. 20.

FIG. 21 is a diagram showing analysis results for the time required to remove the fluorescence signal based on the results of FIG. 20.

As a result, as shown in FIGS. 20 and 21, it was found that when microorganisms are hybridized with the degradable PNA probe, the fluorescence signal could be quickly removed from the PNA probe hybridized with the microorganism's target RNA within about 1 minute after the fluorescence image analysis by simply treating the same with the TCEP solution, without any process to separate the PNA probe hybridized with the microorganism's target RNA (e.g., washing using an organic solvent). In addition, compared to the FISH analysis method that performs photobleaching by irradiating a strong laser to remove the fluorescence signal, the degradable PNA probe-based FISH analysis method was able to remove the fluorescence signal at a faster rate.

The results of this example suggest that the degradable PNA probe-based FISH analysis method can detect or identify one or more types of microorganisms from a sample in which multiple types of microorganisms are mixed in a shorter time compared to the conventional FISH analysis method. Furthermore, the significant reduction in analysis time suggests that the efficiency of multi-FISH analysis can be significantly increased, leading to higher analysis accuracy. In addition, when performing the degradable PNA probe-based FISH analysis, since there is no need to perform strong laser irradiation to remove the fluorescence signal, damage to the sample can be fundamentally prevented.

Example 11. Multiple FISH Analysis Based on Degradable PNA Probe 11.1. Multiple FISH Analysis for Detection or Identification of Single Microorganism Species In the case where sequences of microorganism species are very similar even if they are not identical, one species of a probe is not enough to accurately detect or identify microorganisms of only a single species. For example, when *E. coli* and *S. enterica* each include very similar sequences that are either identical to the sequence targeted by a particular probe or differ by about 1 bp or more, it is likely that a single FISH analysis with the particular probe could not clearly distinguish between the two species. In addition, one of the problems of the FISH analysis method of detecting or identifying a single species of microorganisms based on imaging is that background signals, noise, and non-target microorganisms may be mistakenly recognized as target microorganisms.

Therefore, in this example, in order to detect or identify a single species of microorganisms in a sample, multiplex FISH analysis using several species of biodegradable PNA probes was performed.

Figure 22:
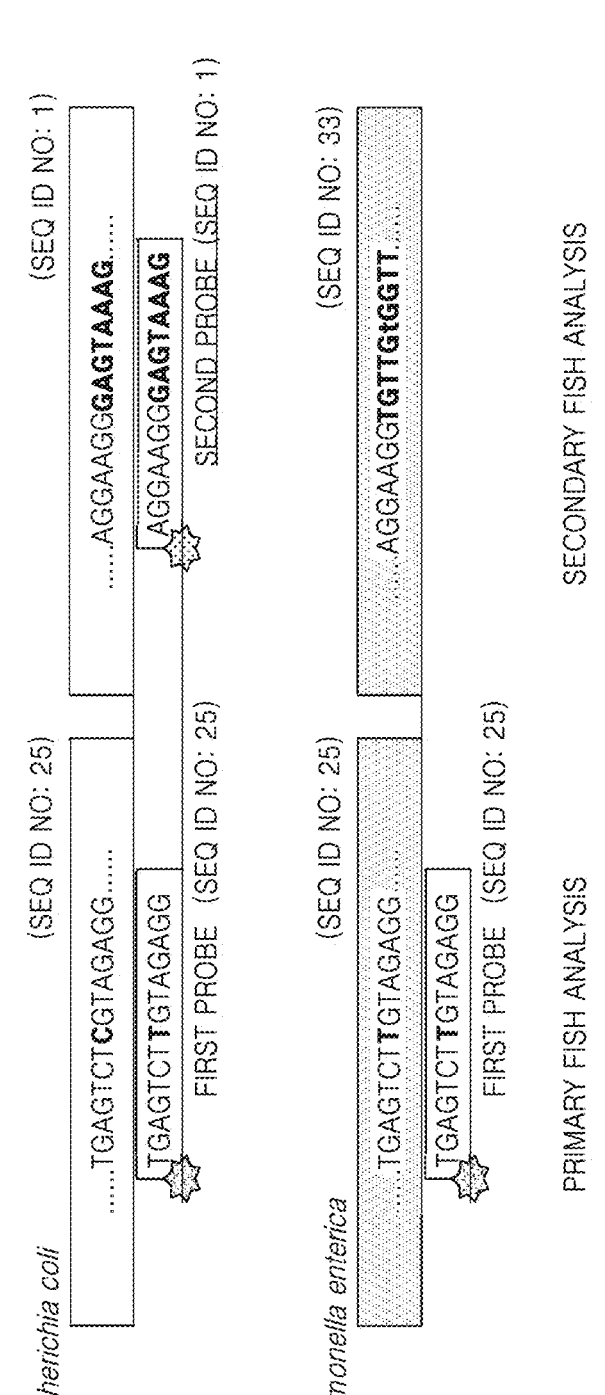
FIG. 22 is a diagram showing a process in which a single species of microorganisms are detected through multiple FISH analysis in which FISH analysis is sequentially repeated using several types of degradable PNA probes.

FIG. 22 is a diagram showing a process in which a single species of microorganisms are detected through multiple FISH analysis in which FISH analysis is sequentially repeated using several types of degradable PNA probes.

In an embodiment, as shown in FIG. 22, in the same manner as in Example 8, the microorganisms of the sample were subjected to concentration, fixation, and permeabilization, and then primary hybridization was performed with the first probe for about 5 minutes. Thereafter, the microorganisms were washed to remove probes that did not hybridize with the target species, and the designated area was imaged by confocal microscopy. Thereafter, the fluorescent material was separated from the probe hybridized with the target species by treatment with about 100 mM TCEP solution for about 1 minute, and the same area was imaged and it was found that the fluorescence signal disappeared. Then, a secondary hybridization was performed using a second probe and this process was repeated. Both the first probe and the second probe are *E. coli* 16s rRNA-specific degradable PNA probes. However, the two types of probes have different target sequences within *E. coli* 16s rRNA.

Figure 23:
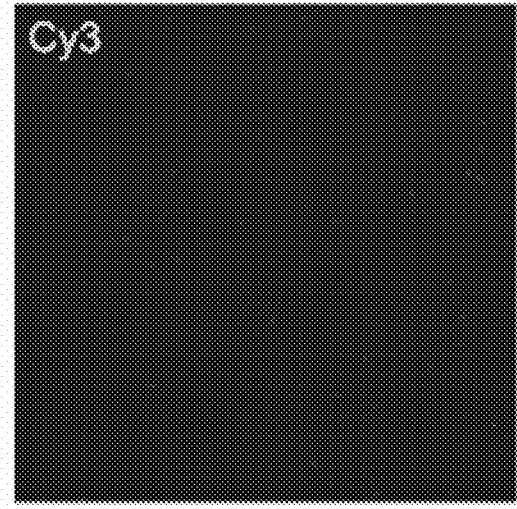
FIG. 23 is a diagram showing results for the detection of a single species of microorganisms through multiple FISH analysis in which FISH analysis is sequentially repeated using several types of degradable PNA probes.
Figure 23:
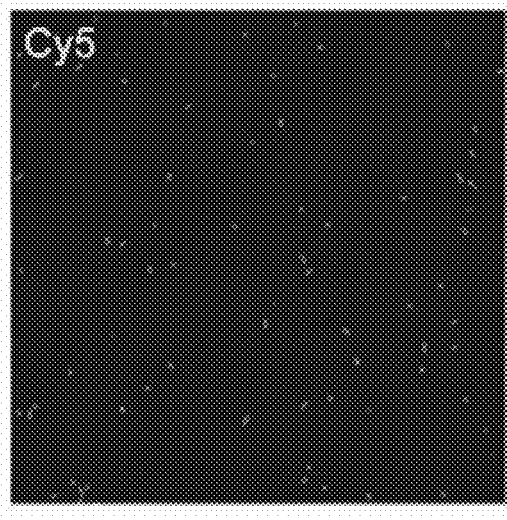

FIG. 23 is a diagram showing results for the detection of a single species of microorganisms through multiple FISH analysis in which FISH analysis is sequentially repeated using several types of degradable PNA probes.

Figure 24:
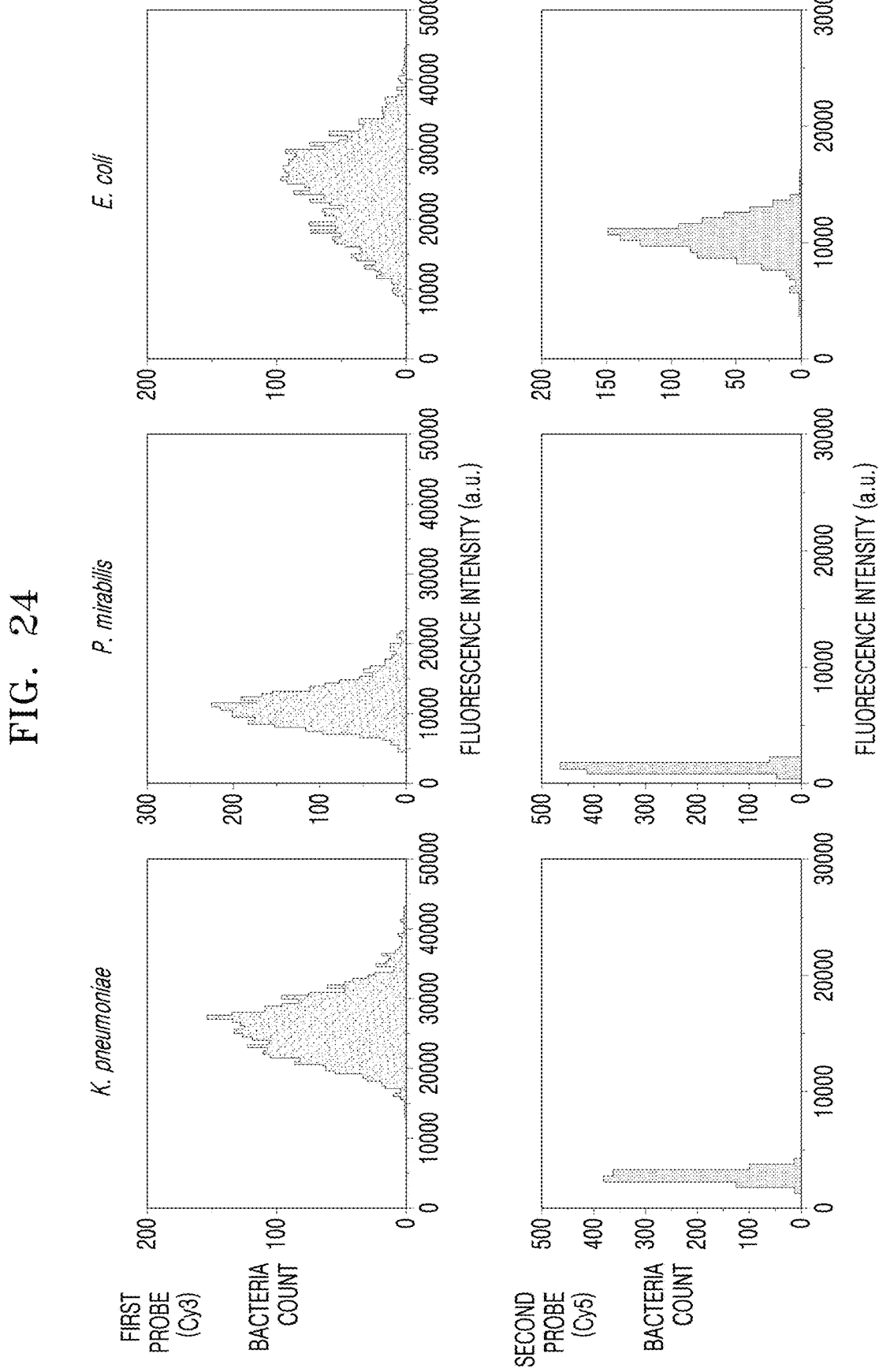
FIG. 24 is a graph showing the quantitative analysis results of the results of FIG. 23.

FIG. 24 is a graph showing the quantitative analysis results of the results of FIG. 23.

As a result, as shown in FIGS. 23 and 24, in the primary FISH analysis, it was found that the first probe labeled with Cy3 hybridizes not only with *E. coli* but also with *K. pneumoniae* and *P. mirabilis* to emit fluorescence signals, emitting fluorescent signals, confirming that the microbial species were not able to be accurately distinguishable from each other. On the other hand, in the secondary FISH analysis, when a second probe labeled with Cy5 was used in the same sample used in the primary FISH analysis, a fluorescence signal emitted by specifically hybridizing with *E. coli* could be confirmed, confirming that the microbial species were able to be accurately distinguishable from each other.

The present example demonstrates that when performing a multiple FISH analysis using two or more probes sequentially targeting each of two or more specific regions containing a single species of microorganisms, the match of the detected microbial species can be reconfirmed in each cycle of the multiple FISH analysis. This result shows that only a single type of microorganisms can be accurately detected or identified in a sample in which several types of microorganisms are mixed through the multiple FISH analysis, and the detection error probability can be significantly reduced.

In addition, according to this example, by using the degradable PNA probe in the multiple FISH analysis, the hybridization time between microorganisms and the probe can be remarkably shortened, and the fluorescence signal of the hybridized probe can be quickly removed, thereby significantly reducing the time required to repeat the process of detecting the fluorescence signal of a new probe.

As a result, the results of the present example suggest that performing a multiple FISH analysis using two or more sequentially degradable PNA probes to detect a single species of microorganisms can significantly shorten the analysis time compared to a conventional FISH analysis while exhibiting significantly better analysis accuracy, thereby significantly increasing the analysis efficiency.

11.2. Multiple FISH Analysis for Detection or Identification of Multiple Microorganism Species In order to detect or identify a plurality of two or more microbial species within the sample, multiple FISH analysis using several degradable PNA probes was performed.

Figure 25:
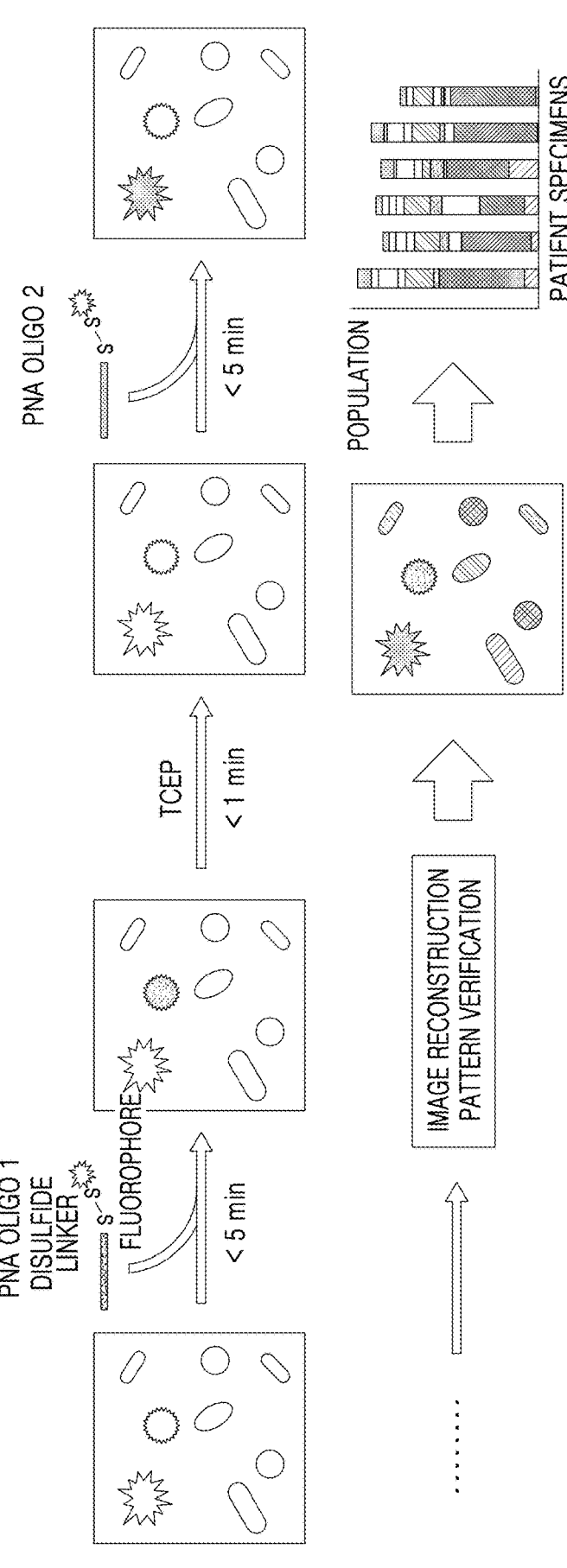
FIG. 25 is a diagram showing a process in which a plural species of microorganisms are detected through multiple FISH analysis in which FISH analysis is sequentially repeated using several types of degradable PNA probes.

FIG. 25 is a diagram showing a process in which a plural species of microorganisms are detected through multiple FISH analysis in which FISH analysis is sequentially repeated using several types of degradable PNA probes.

In an embodiment, as shown in FIG. 25, in the same manner as in Example 8, the microorganisms of the sample were subjected to concentration, fixation, and permeabilization, and then primary hybridization was performed with *S. aureus* 16s rRNA specific degradable PNA probe for about 5 minutes. Thereafter, the microorganisms were washed to remove probes that did not hybridize with the target species, and the designated area was imaged by confocal microscopy. Thereafter, the fluorescent material was separated from the probe hybridized with the target species by treatment with about 100 mM TCEP solution for about 1 minute, and the same area was imaged and it was found that the fluorescence signal disappeared. Then, a secondary hybridization was performed using *E. coli* 16s rRNA specific degradable PNA probe and this process was repeated.

Figure 26:
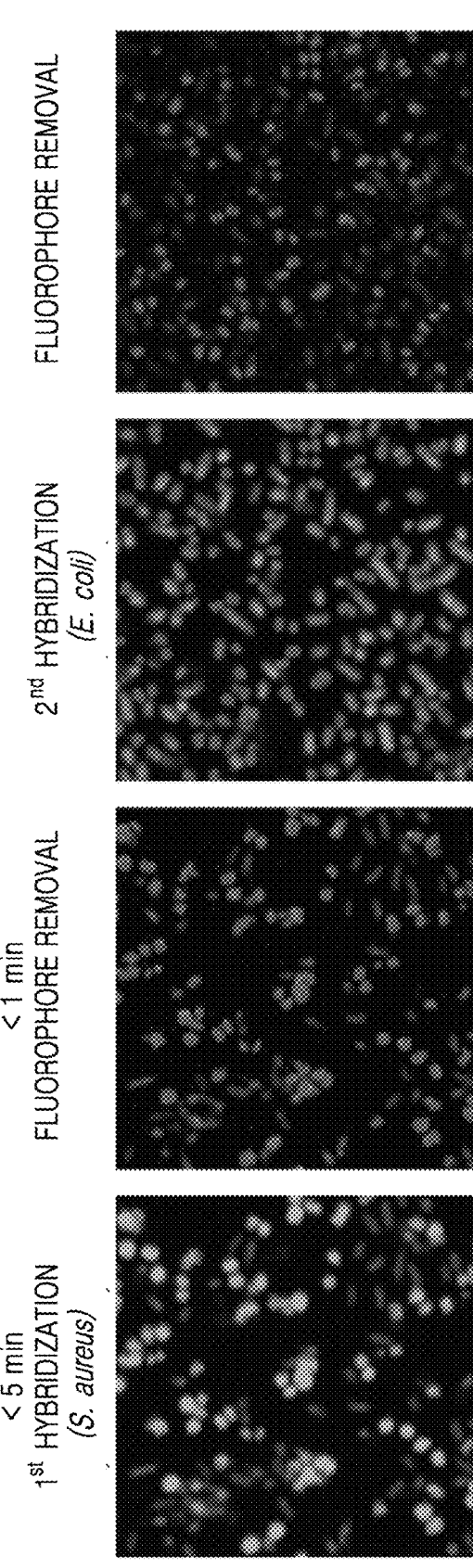
FIG. 26 is a diagram showing results for the detection of a plural species of microorganisms through multiple FISH analysis in which FISH analysis is sequentially repeated using several types of degradable PNA probes.

FIG. 26 is a diagram showing results for the detection of a plural species of microorganisms through multiple FISH analysis in which FISH analysis is sequentially repeated using several types of degradable PNA probes.

Figure 27:
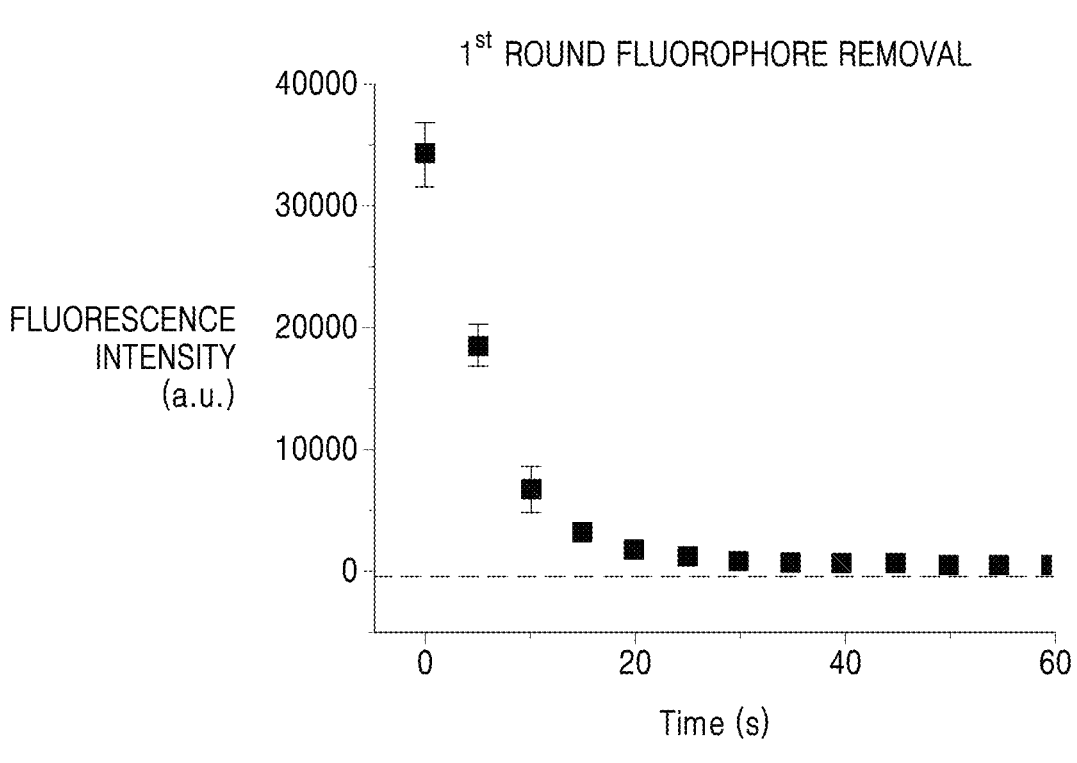
FIG. 27 is a graph showing the result of analyzing the time required to remove the fluorescence signal after detecting the microbial-specific fluorescence signal in FISH analysis of each cycle based on the results of FIG. 26.
Figure 27:
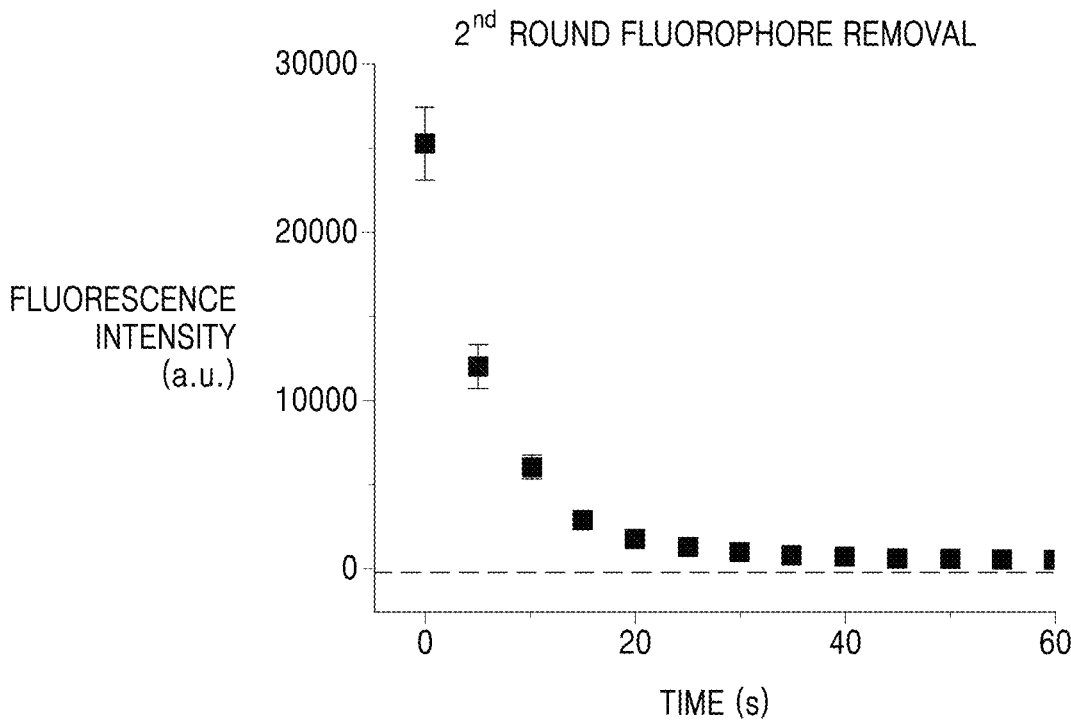

FIG. 27 is a graph showing the result of analyzing the time required to remove the fluorescence signal after detecting the microbial-specific fluorescence signal in FISH analysis of each cycle based on the results of FIG. 26.

As a result, as shown in FIGS. 26 and 27, when multiple FISH analysis based on degradable PNA probes of several species is performed, the fluorescence signal of the probe hybridized with microorganisms was able to be quickly removed in a short time of less than about 1 minute after the detection is finished. As a result, the process of detecting fluorescent signals from probes targeting different microbial species can be quickly repeated, allowing for very rapid detection or identification of a plurality of two or more microbial species.

The results of the present example indicate that multiple FISH analysis based on the degradable PNA probe can rapidly detect each of two or more plurality of microbial species sequentially within a single slide sample, as each cycle of FISH analysis with different target species can be repeated very quickly, as described above. This eliminates the challenges of traditional FISH analysis and maximizes detection efficiency for targeted microorganisms in samples.

Since the specific parts of the present disclosure have been described in detail above, it is clear that these specific descriptions are merely preferred embodiments for those skilled in the art, and the scope of the present disclosure is not limited thereto. Accordingly, the substantial scope of the invention will be said to be defined by the appended claims and their equivalents.

The invention claimed is:

1. A multi-detection method for microorganisms comprising:
   concentrating or fixing microorganisms contained in a sample by contacting the sample and magnetic particles to each other so that the microorganisms included in the sample bind to the magnetic particles; and
   performing fluorescence in situ hybridization on the fixed or concentrated microorganism by detecting signals from a labeled probe.

2. The method of claim 1, wherein the sample is a biological sample, an environmental sample, or a food sample.

3. The method of claim 1, wherein a microbial attachment factor is coated on the surface of each of the magnetic particles.

4. The method of claim 3, wherein the microbial attachment factor comprises at least one selected from the group consisting of mannose binding lectin (MBL), C-reactive protein (CRP), opsonin, CD14, toll-like receptor 4 (TLR4), neutrophil extracellular trap (NET), and a cytokine receptor.

5. The method of claim 1, wherein a magnetic field is applied to the sample including the microorganisms bonded with the magnetic particles to fix the microorganisms.

6. The method of claim 1, wherein the detecting the signals comprises, after detecting a signal emitted from one probe hybridized with microorganisms and before hybridizing another probe, washing the one probe.

7. The method of claim 6, wherein the washing is performed using a solution containing formamide.

8. The method of claim 1, wherein the labeled probe is labeled with a fluorescent material, a chromogenic substance, or a chemiluminescent substance.

9. The method of claim 8, wherein the fluorescent material comprises one or more types of fluorescent materials selected from the group consisting of FAM, VIC, HEX, Cy5, Cy3, SYBR Green, DAPI, TAMRA, FITC, RITC, Rhodamine, Fluoredite, FluorePrime, and ROX.

10. The method of claim 1, wherein the probe is an antibody, an aptamer, DNA, RNA, peptide nucleic acid (PNA), an oligosaccharide, a peptide, or a protein.

11. The method of claim 1, wherein the method is performed in a well, a channel, a tube, or a combination thereof.

12. The method of claim 1, not comprising culturing microorganisms or amplifying a genetic material of microorganisms.

13. The method of claim 1, wherein the microorganisms comprise a bacterium, a virus, a mold, a fungus, or a combination thereof.

14. A method of providing information on diagnosis of infectious diseases, the method comprising:
   concentrating or fixing microorganisms contained in a sample by contacting the sample and magnetic particles to each other so that the microorganisms included in the sample bind to the magnetic particles; and
   performing fluorescence in situ hybridization on the fixed or concentrated microorganism by detecting signals from a labeled probe.

15. The method of claim 14, further comprising determining the presence or absence of microorganisms or the type of microorganisms, by using information about the probe from which the signal is emitted.

* * * * *